US009233364B2

(12) United States Patent
Murray et al.

(10) Patent No.: US 9,233,364 B2
(45) Date of Patent: Jan. 12, 2016

(54) MULTIMETALLIC ASSEMBLY, METHODS OF MAKING MULTIMETALLIC ASSEMBLY, METHODS OF OXIDIZING WATER, METHODS OF O-ATOM TRANSFER CATALYSTS, AND METHODS OF CARBON DIOXIDE REDUCTION

(71) Applicant: University of Florida Research Foundation, Inc., Gainesville, FL (US)

(72) Inventors: Leslie Justin Murray, Gainesville, FL (US); Gary Louis Guillet, Gainesville, FL (US); Gianna Nadine Di Francesco, Gainesville, FL (US); Jesse B. Gordon, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 338 days.

(21) Appl. No.: 13/870,041

(22) Filed: Apr. 25, 2013

(65) Prior Publication Data

US 2013/0287671 A1  Oct. 31, 2013

Related U.S. Application Data

(60) Provisional application No. 61/637,906, filed on Apr. 25, 2012.

(51) Int. Cl.
*B01J 31/22* (2006.01)
*C01B 31/00* (2006.01)
(Continued)

(52) U.S. Cl.
CPC ............ *B01J 31/2295* (2013.01); *B01J 31/183* (2013.01); *B01J 31/2273* (2013.01); *C01B 31/00* (2013.01); *C07F 1/08* (2013.01); *C07F 9/505* (2013.01); *C07F 9/5022* (2013.01); *C07F 9/5325* (2013.01); *C07F 15/025* (2013.01);
(Continued)

(58) Field of Classification Search
CPC ...... C01B 15/01; C01B 31/00; B01J 31/2295; B01J 223/625; B01J 2231/70; B01J 2531/0244; C07F 9/505; C07F 9/5022; C07F 9/5325; C07F 15/025; C07F 15/04
USPC ............ 546/12; 568/14; 423/415.1, 579
See application file for complete search history.

(56) References Cited

U.S. PATENT DOCUMENTS 5,936,029 A * 8/1999 Hall ........................ 524/572
6,054,580 A   4/2000 Collins et al.
(Continued)

FOREIGN PATENT DOCUMENTS

CN   101259437   9/2008
WO   2010143663  12/2010

OTHER PUBLICATIONS

Machado, et al. Review: Self-Assembly in Self-Organized Inorganic Systems: A view of Programmed Metallosupramolecular Architectures, Journal of the Brazilian Chemical Society, Aug. 2001, pp. 431-462, 12(4).
(Continued)

*Primary Examiner* — Timothy Vanoy
(74) *Attorney, Agent, or Firm* — Thomas Horstemeyer, LLP

(57) ABSTRACT

Embodiments of the present disclosure provide for multimetallic assemblies, methods of making a multimetallic assembly, methods of oxidizing water, methods of O-atom transfer catalysis, and the like.

14 Claims, 13 Drawing Sheets
(5 of 13 Drawing Sheet(s) Filed in Color)

(51) Int. Cl.
  C07F 9/50    (2006.01)
  C01B 13/00   (2006.01)
  C07F 9/53    (2006.01)
  C07F 15/02   (2006.01)
  C07F 15/04   (2006.01)
  C07F 1/08    (2006.01)
  B01J 31/18   (2006.01)

(52) U.S. Cl.
  CPC ............ *C07F 15/04* (2013.01); *B01J 2231/625* (2013.01); *B01J 2231/70* (2013.01); *B01J 2531/0216* (2013.01); *B01J 2531/0244* (2013.01); *B01J 2531/16* (2013.01); *B01J 2531/842* (2013.01)

(56) References Cited

U.S. PATENT DOCUMENTS

| | | |
|---|---|---|
| 6,596,259 B1 | 7/2003 | Raptis |
| 6,803,474 B1 | 10/2004 | Dismukes et al. |
| 7,060,818 B2 | 6/2006 | Horwitz et al. |
| 2009/0062110 A1 | 3/2009 | Koshino et al. |
| 2009/0062498 A1 | 3/2009 | Matzger et al. |
| 2009/0306368 A1 | 12/2009 | Sugiyama et al. |
| 2010/0129698 A1 | 5/2010 | Okada et al. |
| 2010/0197886 A1 | 8/2010 | Ishiyama et al. |
| 2010/0210451 A1 | 8/2010 | Busch et al. |
| 2011/0028310 A1 | 2/2011 | Busch et al. |
| 2013/0066029 A1* | 3/2013 | Radlauer et al. .............. 526/171 |

OTHER PUBLICATIONS

Mateus, et al., A Trinuclear Copper (II) Cryptate and Its µ3-CO3 Cascade Complex: Thermodynamics, Structural and Magnetic Properties. Chemistry—A European Journal, 2011, pp. 11193-11203, 17(40).

Lusby, Paul J., Supramolecular coordination chemistry, Annual Reports Section A: Inorganic Chemistry, May 26, 2011, 107, pp. 297-318.

Jiang and Chen, Recent developments in synthesis and applications of triptycene and pentiptycene derivatives, European Journal of Organic Chemistry 2011, 32, pp. 6377-6403.

Chen, Chuang-Feng, Novel Triptycene-Derived Hosts: Synthesis and Their Applications in Supramolecular Chemistry, Chemical Communications, 2011, 47, pp. 1674-1688.

\* cited by examiner

X = cap

Y = arm

Z = connecting atom type where YZ$_2$ constitutes an arm for metal binding, and X constitutes a cap which may/may not coordinate a metal center n = 2 or 3

Z = NH, NR, O, S, CH, CR, CH$_2$
R = alkyl or aryl group
R' = NO$_2$, H, alkyl, aryl, CF$_3$, OMe, COOR
A = CH or N

YZ$_2$ = n = 1 to 20 or 1 to 10 n = 2 or 3

X = cap

Y = arm

Z = connecting atom type where $YZ_2$ constitutes an arm for metal binding, and X constitutes a cap which may/may not coordinate a metal center Z = NH, NR, O, S, CH, CR, $CH_2$
R = alkyl or aryl group
R' = $NO_2$, H, alkyl, aryl, $CF_3$, OMe, COOR
A = CH or N
LG = OH, OR, halide, RCOO, OTf $YZ_2$ = n = 2 or 3

X = cap
Y = arm
Z = connecting atom type
where YZ$_2$ constitutes an arm for metal binding, and X constitutes a cap which may/may not coordinate a metal center Z = NH, NR, O, S, CH, CR, CH$_2$
R = alkyl or aryl group
R' = NO$_2$, H, alkyl, aryl, CF$_3$, OMe, COOR
A = CH or N

YZ$_2$ =

1

2

X = cap
Y = arm
Z = connecting atom type
n = 2 or 3

R₁ = H, alkyl, aryl, alkylether
R₂ = H, alkyl, aryl, carboxylate, NO₂
A = CH or N

X =

Scheme 1. Synthesis of the multidentate cryptand, H₆L. (*i*) SOCl₂, MeOH (*ii*) EtI, NaH, DMF, (*iii*) HNO₃, TFA (*iv*) Raney Ni, H₂(g), THF/EtOH

MULTIMETALLIC ASSEMBLY, METHODS OF MAKING MULTIMETALLIC ASSEMBLY, METHODS OF OXIDIZING WATER, METHODS OF O-ATOM TRANSFER CATALYSTS, AND METHODS OF CARBON DIOXIDE REDUCTION

CLAIM OF PRIORITY TO RELATED APPLICATION

This application claims priority to co-pending U.S. provisional application entitled "MULTIMETALLIC ASSEMBLY, METHODS OF MAKING MULTIMETALLIC ASSEMBLY, METHODS OF OXIDIZING WATER, AND METHODS OF O-ATOM TRANSFER CATALYSTS" having Ser. No. 61/637,906, filed on Apr. 25, 2012, which is entirely incorporated herein by reference.

BACKGROUND

The design of synthetic catalysts to replicate the reactivity of metalloproteins is a long standing research goal with substantial focus on the synthesis and properties of metal complexes that are structural mimics of enzymatic metal clusters. However, these structural analogues have yet to operate as effective catalysts for multielectron redox reactions. Thus, there is a need to develop metal complexes that can mimic enzymatic metal clusters.

SUMMARY

Embodiments of the present disclosure provide for multimetallic assemblies, methods of making a multimetallic assembly, methods of oxidizing water, method of reducing carbon dioxide, methods of O-atom transfer catalysis, and the like.

In an embodiment, a multimetallic assembly, among others, includes:

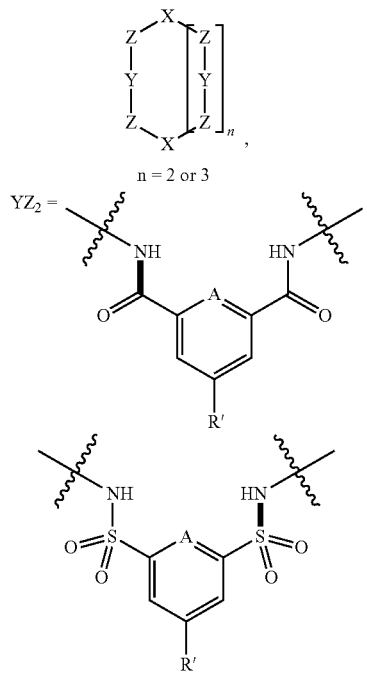

-continued

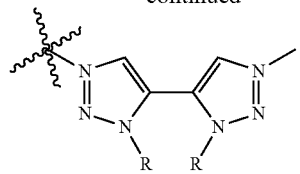

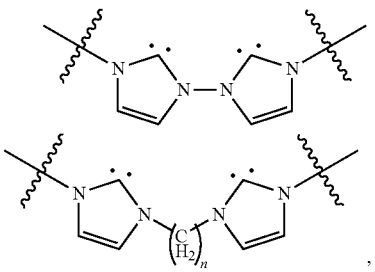

$X =$

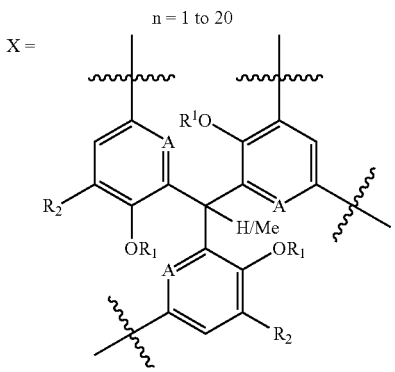

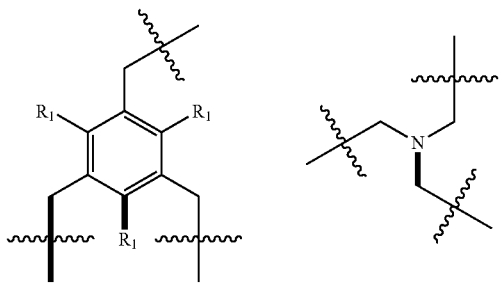

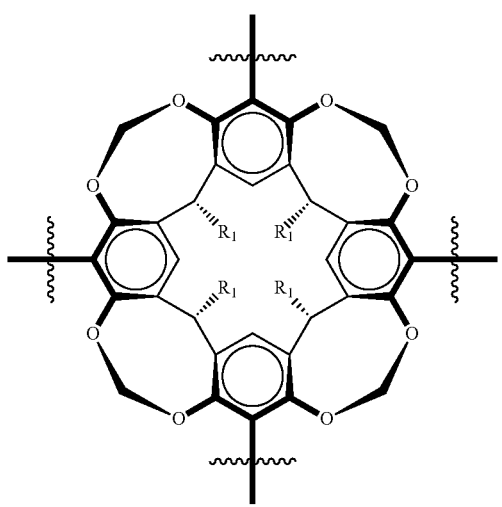

-continued

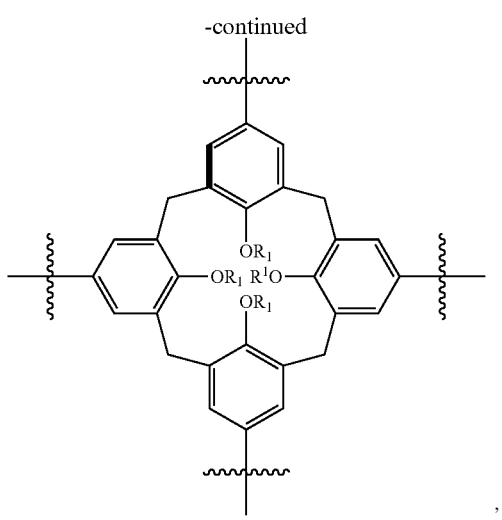

, wherein Z is NH, NR, O, S, CH, CR, or $CH_2$; R and R' are independently selected from an alkyl group, an aryl group, $NO_2$, H, a substituted alkyl, a cycloalkyl, a substituted cycloalkyl, a substituted aryl, a heteroaryl, a substituted heteroaryl, a sulfonate, a sulfonyl ester, a carboxylate, an ester, $CF_3$, OMe, or $COOR_1$; A is CH or N; $R_1$ and $R_2$ are independently selected from H, alkyl group, an aryl group, a carboxylate, $NO_2$, a substituted alkyl, a cycloalkyl, a substituted cycloalkyl, a substituted aryl, a heteroaryl, a substituted heteroaryl, sulfone, sulfonate, a sulfonyl ester, a carboxylate, $CF_3$, OMe, or ester.

In an embodiment, a method of oxidizing water, among others, includes: exposing the water to a multimetallic assembly as described herein.

In an embodiment, a method of reducing carbon dioxide, among others, includes: exposing the carbon dioxide to a multimetallic assembly as described herein.

In an embodiment, a method of O-atom transfer, among others, includes: exposing $O_2$ or a reactive oxygen species to a multimetallic assembly as described herein: and reacting the product of step one with an electron-rich substrate to transfer the O-atom to the electron-rich substrate.

Other structures, compositions, methods, features, and advantages will be, or become, apparent to one with skill in the art upon examination of the following drawings and detailed description. It is intended that all such additional structures, systems, methods, features, and advantages be included within this description, be within the scope of the present disclosure, and be protected by the accompanying claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 9A and 9B describe embodiments of the present disclosure, while

DISCUSSION

Figure 1:
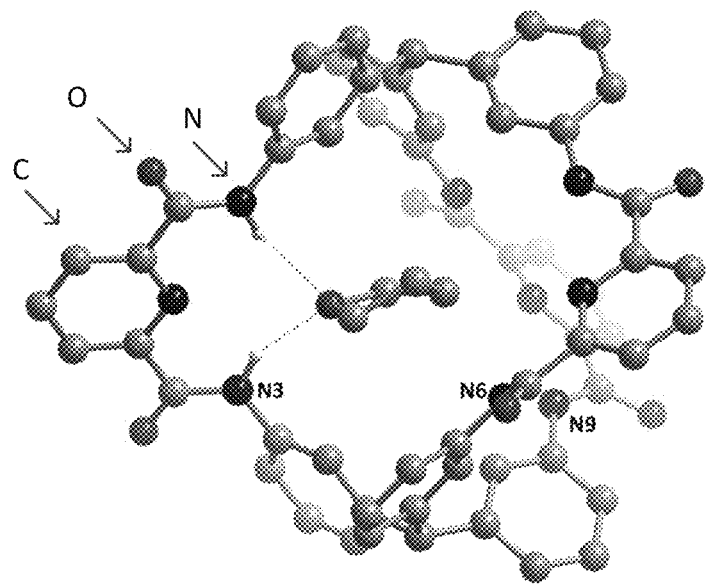
FIG. 1 illustrates a portion of the crystal structure of $H_6L.(THF)_3.(H_2O)_3$.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed. Terms defined in references that are incorporated by reference do not alter definitions of terms defined in the present disclosure or should such terms be used to define terms in the present disclosure they should only be used in a manner that is inconsistent with the present disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, material science, physics, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmosphere. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

The term "substituted" refers to any one or more hydrogens on the designated atom that can be replaced with a selection from the indicated group, provided that the designated atom's normal valence is not exceeded, and that the substitution results in a stable compound.

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, and s-pentyl. The term "lower alkyl" means an alkyl group having less than 10 carbon atoms.

The term "substituted," as in "substituted alkyl", "substituted cycloalkyl," "substituted aryl," "substituted heteroaryl" and the like means that the substituted group may contain in place of one or more hydrogens a group such as hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "cycloalkyl" refers to a non-aromatic mono- or multicyclic ring system of about 3 to about 10 carbon atoms, preferably of about 5 to about 10 carbon atoms. Preferred ring sizes of rings of the ring system include about 5 to about 6 ring atoms. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl. Preferred examples are furanyl, imidazyl, pyranyl, pyrrolyl, and pyridyl.

The term "alkylether" is used herein to refer to R1-O—R2, where one of R1 and R2 is selected from an alkyl group.

Discussion

Embodiments of the present disclosure provide for multimetallic assemblies, methods of making a multimetallic assembly, methods of oxidizing water, methods of reducing carbon dioxide, methods of O-atom transfer catalysis, and the like. Exemplary embodiments of the present disclosure include multimetallic assemblies that can be multi-metallic nuclearity complexes (e.g., trimetallic or higher nuclearity complexes). Exemplary embodiments of the present disclosure have macrocyclic organic architectures that are modular and can be readily tuned to vary the electronic environment of the metal, which is an important feature for designing multimetallic assemblies in various applications (e.g., catalyst design/development). Additional details are provided herein and in the Examples.

Embodiments of the present disclosure are advantageous over current approaches in that they require less energy, are less expensive reaction equipment, and that they are require less costly safety mechanisms. In particular, current approaches for utilizing small molecules as feed-stocks for chemical synthesis, such as the Haber-Bosch Process, are typically energy intensive and require costly safety mechanisms and reaction equipment.

Embodiments of the present disclosure can be used for the activation (e.g., oxidative reaction) of small molecules (e.g., $H_2O$, and $H_2O_2$) that are abundant in the environment such as water, for O-atom transfer (e.g., $O_2$ or from and O-atom donor), and carbon dioxide reduction. In an embodiment, the multimetallic assemblies can find applications in water oxidation, molecular batteries, and molecular magnets. Embodiments of the present disclosure have applications in fine chemical and industrial synthesis and renewable energy technologies. Embodiments of the present disclosure can be used as catalysts and provide routes to value-added commodities with improved energy efficiency and utilize renewable energy sources such as solar or wind power, and mitigate the need for harsh reaction conditions. In particular, embodiment of the present disclosure can have applications in catalysis, by introducing novel Lewis acidity or metal centers with different redox potentials into the complex. In addition, embodiment of the present disclosure can be used in other applications including metal-ion sensors and MRI-contrast agents.

Embodiments of the present disclosure include the synthesis of controlled modular organic scaffolds (e.g., the multimetallic assembly) to support one, two, three, four, or five metal centers, arranged around a central cavity. This central cavity provides a site for binding of potential substrates (e.g., $H_2O$) and their subsequent conversion to products, which either releases energy to carry out work and/or requires energy input, which is chemically stored in the products.

In an embodiment, the multimetallic assembly provides for a family of catalysts with the same or mixed metal composition and site-specific tuning of one or more metal centers. Accessing homometallic systems is straightforward but the ability to carefully define all aspects of these architectures remains difficult. Macrobicyclic ligands (e.g., such as those derived from triphenylmethane-like units) present in the multimetallic assembly provide a well-defined environment that defines the relative orientation of the metal centers, the coordination sphere of each metal, and the accessibility of substrates. In regard to the macrobicyclic ligand such as triphenylmethane-like units, each arm of the macrobicycles can coordinate one metal cation (e.g., the same or different) to afford three symmetrically disposed metal cations. Incorporation of one or two metal cations is possible by building a metal-binding domain into the cap unit. Simply, this approach affords two or more types of metal centers all of which are oriented around a central pocket, allowing each metal to cooperatively react with substrates and effect sequential and rapid electron abstraction. Embodiments of the present disclosure provide for a large number of two-fold, three-fold, or more symmetric multimetallic assemblies that can be accessed by changing only the precursor to the metal-binding arm (e.g., Y in FIGS. 9A, 9B, and 9C). In an embodiment, the multimetallic assembly can include the three distinct types of metal coordination environments with the five metal centers.

In an embodiment, the multimetallic assembly can be asymmetric to tune the performance of the system or introduce new functionality. For example, one distinct metal binding arm can be incorporated into the ligand by taking advantage of the synthetic flexibility afforded by the macrobicyclic ligand (e.g., triphenylmethane units as well as others shown in FIGS. 9A, 9B, and 9C). In an embodiment, the arm (Y) can be selected to preferentially coordinate a different metal ion to generate a mixed-metal complex or to tune the properties of one metal ion within the complex. These $C_3$-antisymmetric complexes introduce one metal site within the complex with a distinct reactivity from other metal centers in the complex.

Now having described embodiments of the present disclosure in general, the following provides more details regarding embodiments of the multimetallic assembly. As noted above, embodiments of the present disclosure include multimetallic assemblies that are multi-metallic nuclearity complexes. Exemplary embodiments of the present disclosure have macrocyclic organic architectures that are modular and can be readily tuned to vary the electronic environment of the metal. Thus, the various parts (e.g., X, Y, Z (and $YZ_2$), R, R', A, $R_1$, $R_2$, and LG) of the structures shown in FIGS. 9A and 9B can be selected to design the desired multimetallic assembly.

Figure 9A:
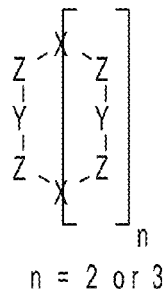
Figure 9A:
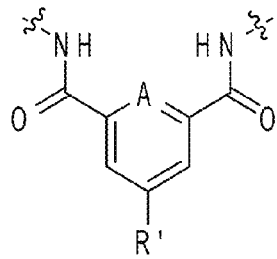
Figure 9A:
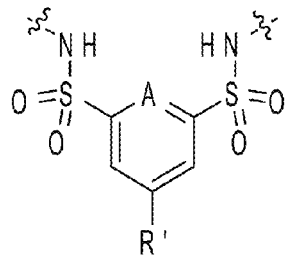
Figure 9A:
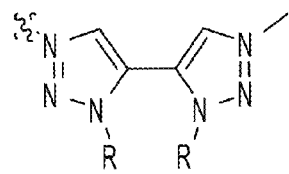
Figure 9A:
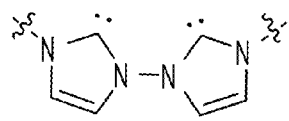
Figure 9A:
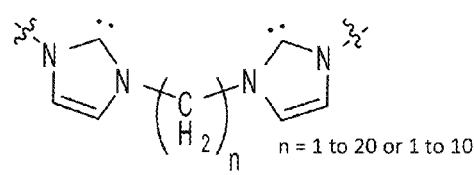
Figure 9B:
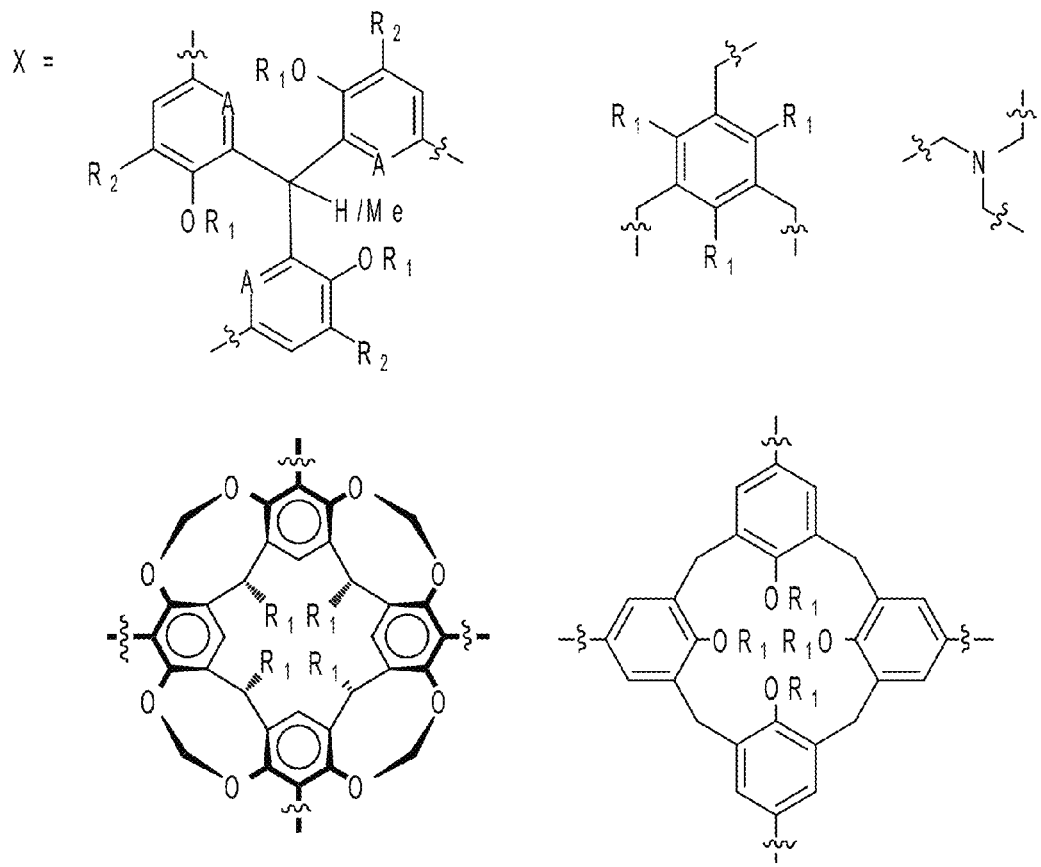
Figure 9C:
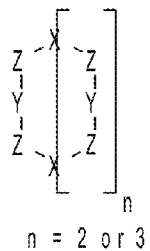
FIG. 9C illustrates an exemplar method for making embodiments of the multimetallic assembly.
Figure 9C:
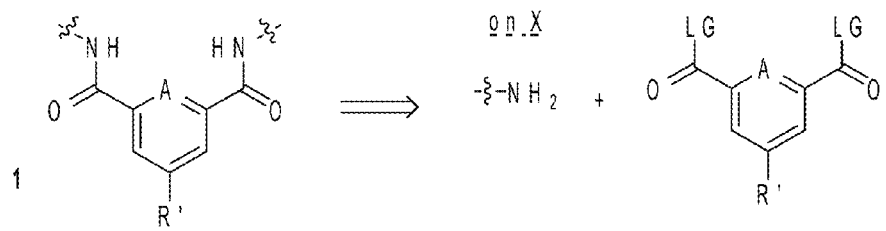
Figure 9C:
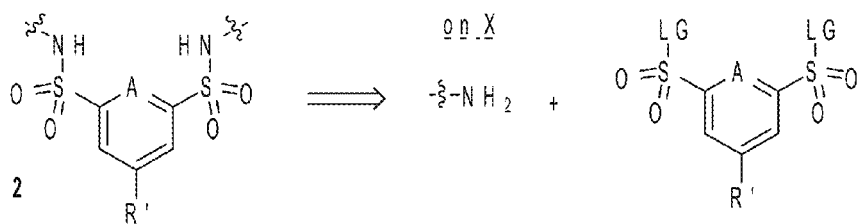
Figure 9C:
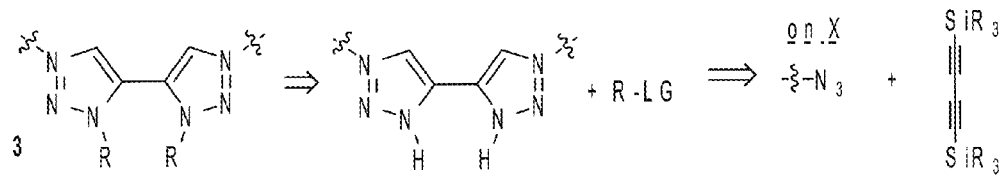
Figure 9C:
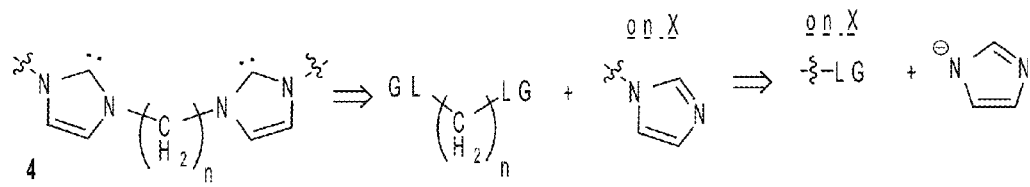

FIGS. 9A and 9B describe embodiments of the present disclosure, while FIG. 9C illustrates an exemplar method for making embodiments of the multimetallic assembly. X, Y, and Z (and $YZ_2$) are described in FIGS. 9A and 9B. FIGS. 9E and 9F describe additional embodiments. X is a cap that can coordinate to a metal center. Y is an arm and Z is an atom or group that connects Y to X. $YZ_2$ is an arm for metal binding. Embodiments of R, R', A, $R_1$, $R_2$, and LG are described in FIGS. 9A, 9B, 9C, 9E and 9F. In an embodiment, Z can be NH, NR, O, S, CH, CR, or $CH_2$. In an embodiment, R can be an alkyl group or an aryl group. In an embodiment, R' can be $NO_2$, H, an alkyl group, an aryl group, $CF_3$, OMe, or $COOR_1$. In an embodiment, A can be CH or N. In an embodiment, R and R' can also independently include a substituted alkyl, a cycloalkyl, a substituted cycloalkyl, a substituted aryl, a heteroaryl, a substituted heteroaryl, sulfonate, sulfonyl esters, carboxylate, ester, and the like. In an embodiment, $R_1$ and $R_2$ can also independently include a substituted alkyl, a cycloalkyl, a substituted cycloalkyl, a substituted aryl, a heteroaryl, a substituted heteroaryl, sulfone, sulfonate, sulfonyl esters, carboxylate, ester, and the like. In an embodiment, $YZ_2=1$ (See FIG. 9E), X=1 (See FIG. 9F) with A=CH, $R_1=CH_2CH_3$, $R_2=CH(CH_3)_2$.

In an embodiment the metal(s) associated with the multimetallic assembly can include transition metals (e.g., manganese, iron, cobalt, nickel, copper, vanadium, chromium, palladium, platinum, gold, ruthenium, rhodium, and iridium) and a combination thereof. As mentioned above, an embodiment of the multimetallic assembly can include the same metal, two or more different types of metals, where the metals can be different in oxidation state of the same metal (e.g., Fe(II), Fe(III)) and/or different types of metals (e.g., Fe and Co). The metal(s) can be selected based on the application of the particular multimetallic assembly. Exemplar embodiment is provided in the Examples.

FIG. 9C illustrates an exemplary embodiment of making multimetallic assemblies, such as those described in reference to FIGS. 9A and 9B. $YZ_2$ and X can be made using known techniques and one or more of the following references describes how they can be made: Eur. J. Org. Chem. 2011, 6789-6793; J. Org. Chem., 1986, 51 (5), pp 742-745; Nature Protocols 2,-1288-1296 (2007); Synthesis 2005, pp 2080-2083; and J. Chem. Soc., Perkin Trans. 12000, 1741-1748, each of which is incorporated herein by reference.

As noted above, embodiments of the present disclosure can be used to oxidize substrates such as water, and a combination thereof. The following discussion about the oxidation of water is provided as an example, and other substrates can be oxidized considering the same principles.

Figure 9D:
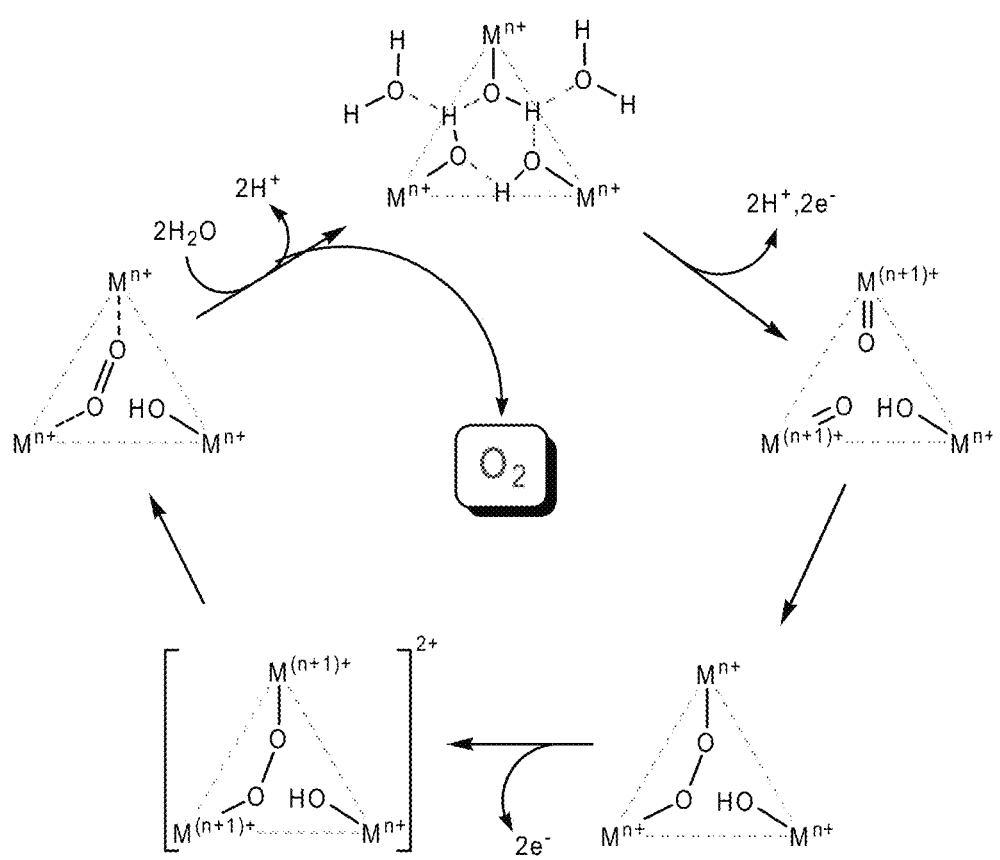
FIG. 9D illustrate complexes that can carry out water oxidation either under electrochemical or photochemical conditions, where the multimetallic assembly is either oxidized directly or through a mediator by an electrode or by an independent photosensitizer molecule.
Figure 9E:
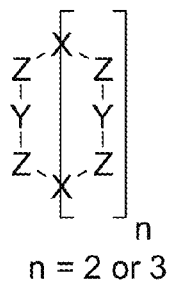
FIGS. 9E and 9F illustrate additional embodiments.
Figure 9E:
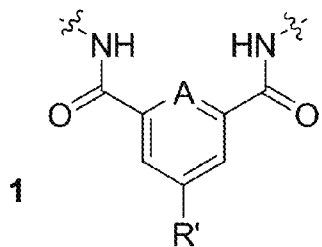
Figure 9E:
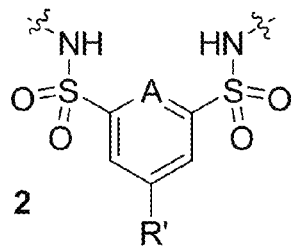
Figure 9F:
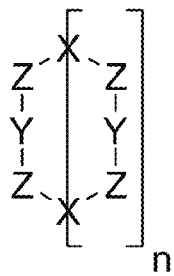
Figure 9F:
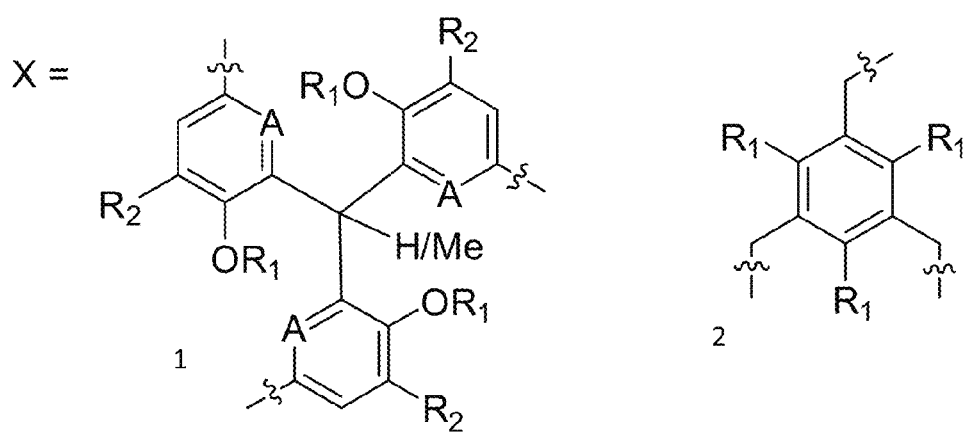

Complexes can carry out water oxidation either under electrochemical or photochemical conditions, where the multimetallic assembly is either oxidized directly or through a mediator by an electrode or by an independent photosensitizer molecule (See FIG. 9D). O—O bond formation can occur either through a radical-type mechanism or through attack of a coordinated hydroxide or solvent water molecule on an electrophilic metal-oxo unit.

As noted above, embodiments of the present disclosure can be used to reduce substrates such as carbon dioxide, and a combination thereof. The following discussion about the carbon dioxide reduction is provided as an example, and other potential pathways in which carbon dioxide is formally reduced can be present.

Figure 11:
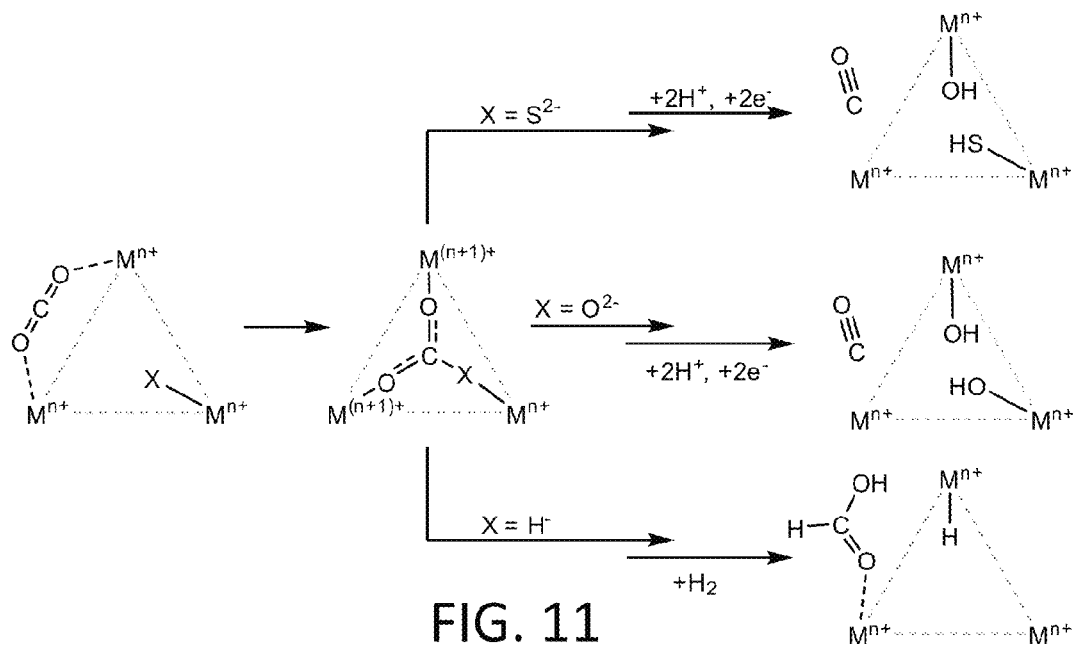
FIG. 11 illustrates a scheme regarding carbon dioxide reduction.

FIG. 11 illustrates a scheme regarding carbon dioxide reduction. Complexes can carry out carbon dioxide reduction either under electrochemical or photochemical conditions, where the multimetallic assembly is either reduced directly or through a mediator by an electrode or by an independent photosensitizer molecule (See FIG. 11). C=O bond cleavage can occur either through a radical-type mechanism or through attack of a coordinated ligand (e.g., hydrosulfide). Alternatively, carbon dioxide reduction can lead to formation of formate, through formal hydride addition to the central carbon atom of $CO_2$.

Figure 12:
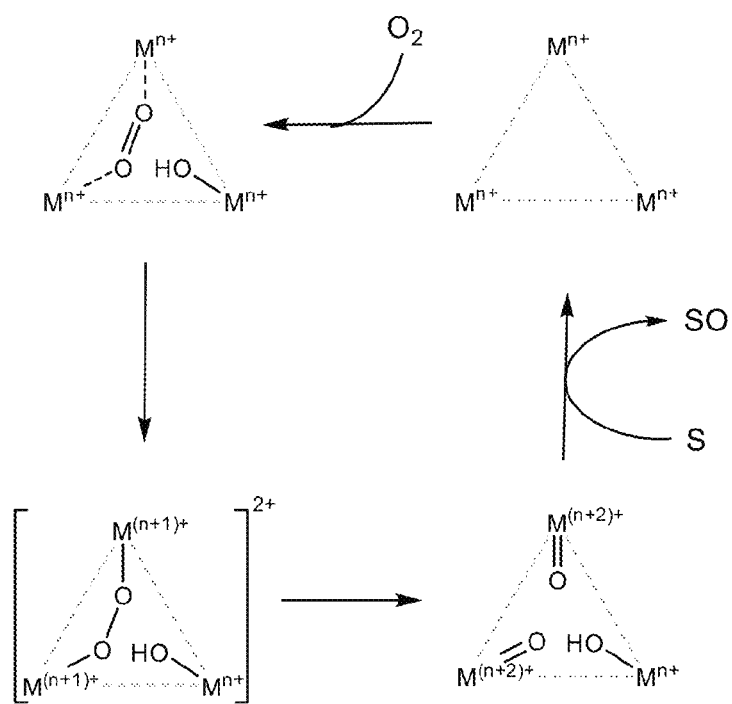
FIG. 12 illustrates a scheme regarding O atom transfer.

FIG. 12 illustrates a scheme regarding O atom transfer. For O-atom transfer, high-valent oxidizing metal-oxo centers can be generated by reaction of reduced complexes with either $O_2$ or other reactive oxygen species (e.g., PhIO, mCPBA, or $H_2O_2$). Subsequent reaction of these high-valent metal-oxo complexes with electron-rich substrates (e.g., alkenes, sulfides) results in transfer of the O-atom to the substrate and concomitant reduction of the metal centers.

EXAMPLES

Now having described the embodiments of the disclosure, in general, the example describes some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Brief Introduction:

Reaction of tris(5-amino-2-ethoxy-3-isopropylphenyl) methane and pyridine-2,6-dicarbonyl-dichloride affords a multi-dentate cryptand in 48% yield. Metallation with iron (III) chloride results in a substantial conformational change of this ligand to give a trianionic triiron(III) complex. Ferric cations line the periphery of the internal cavity with each adopting a square pyramidal $N_3Cl_2$ coordination environment.

Discussion:

Proteins that catalyze multielectron redox reactions combine a tailored active site pocket with multimetallic assemblies, where the metal clusters provide the redox equivalents to drive the reaction, and the active site enforces substrate selectivity.[1] The design of synthetic catalysts to replicate the reactivity of metalloproteins is a long standing research goal with substantial focus on the synthesis and properties of metal complexes that are structural mimics of enzymatic metal clusters. However, these structural analogues[2] have yet to operate as effective catalysts for multielectron redox reactions.[3]

The design of molecular receptors that selectively recognize specific analytes is well-developed in organic synthesis.[4,5] These types of molecules are constructed with a carefully tailored binding site that recognizes the target analyte selectively based on size, as dictated by the shape and volume of the binding site relative to the target molecule, and electrostatic or hydrogen bonding interactions between functional groups incorporated on the interior surface of the binding cavity and complementary groups on the analyte. Metal ions, such as copper(II), have been incorporated into organic receptors, where the metal ion serves as a Lewis acid for analyte recognition rather than as a redox-active catalytic centre.[6] Realizing the interplay between the active site and metal cofactors in enzyme systems, our approach focuses on incorporating multiple metal coordination sites into molecular receptors as a means to combine metal cooperativity with substrate selectivity.

Previously, multimetallic complexes of cofacial diporphyrins, pacman porphyrins, and bis(TREN) cryptands, among others, have been carefully designed to preorganize metal centers around an active site, in which the ligand orients accessible metal coordination sites to react with substrates cooperatively.[7] Rational catalyst design however requires synthetic control of the electronic and structural properties of the metal centres, which cannot be achieve without sacrificing synthetic ease or yield for porphyrin- and TREN-based ligands. Despite these drawbacks, macrobicycles remain attractive candidates because libraries of multimetallic complexes can be readily synthesized using a modular approach. We sought to develop macrobicyclic ligands, in which synthetic precursors with versatile functional groups could be easily accessed. In this regard, tris(2-hydroxyphenyl)methanes are an ideal candidate because the synthesis of these triarylmethanes tolerates various functionalities on the reactant phenol and salicylaldehyde.[8] Here we report the synthesis and metallation of the first cryptand to be synthesized from tris(5-amino-2-ethoxy-3-isopropylphenyl)methane and the corresponding triiron(III) complex. This result demonstrates a route to potentially create tunable ligands for metal clusters by varying the functional groups on the phenols and salicylaldehyde.

Figure 10:
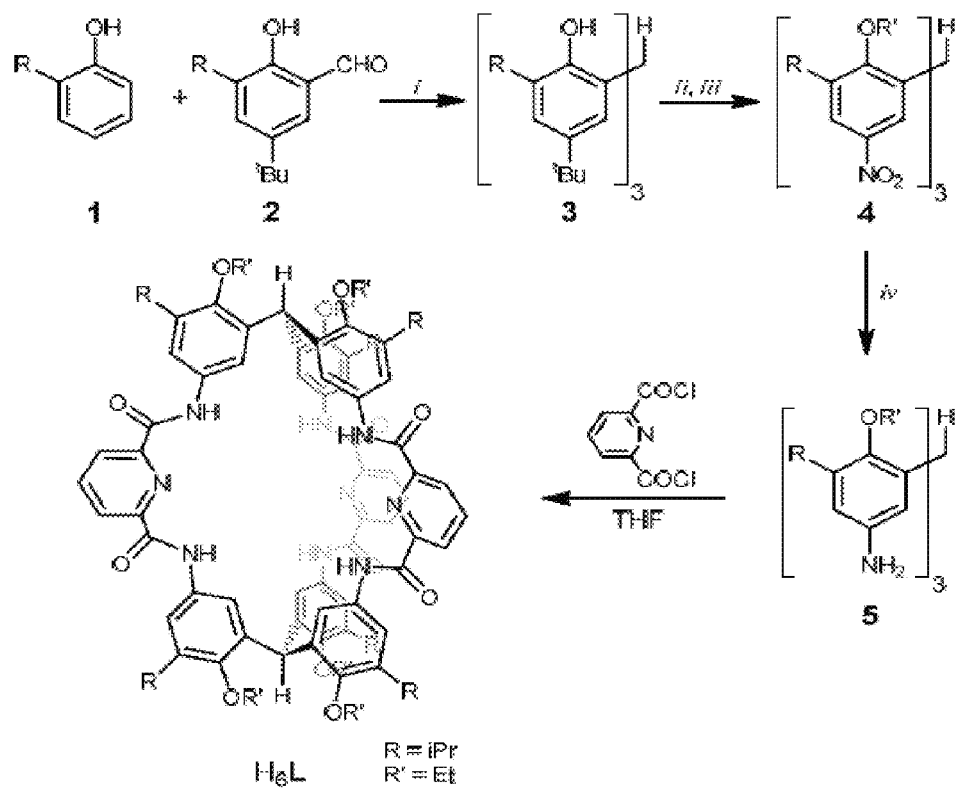
FIG. 10 illustrates Scheme 1, which shows the synthesis of the multidentate cyrptand $H_6L$.

Reaction of phenol 1 and salicylaldehyde 2[8] with thionyl chloride in methanol affords the substituted triphenoxymethane 3 (FIG. 10, Scheme 1).[9] From prior reports, we anticipated that the alkoxy groups would preferentially align to one molecular face with the nitro-substituents in 4 oriented to the opposite face.[9,10] Alkylation followed by nitration afforded 4, and subsequent reduction yielded our desired building block 5 in multigram quantities.[9,11] Ease of purification for each synthetic step compensated for the low overall yield of 5. Condensation of two equivalents of 5 with three of pyridine-2,6-dicarbonyl dichloride afforded the desired cryptand $H_6L$ in 48% yield (FIG. 10, Scheme 1). We attribute the unusually high yield for the final step in our synthetic route to the alignment of the amines to one molecular face, which has been proposed for cyclophanes assembled from 1,3,5-triethylbenzene.[12]

From the single-crystal X-ray structure, the pyridine dicarboxamide arms of $H_6L$ adopt a propeller arrangement and preassemble around a 126 Å$^3$ central cavity (FIG. 1).[13] The distances between the amide nitrogen atoms range from 6.577(4) Å for N6-N3 to 7.130(3) Å for N9-N3. Expectedly, these metrics are similar to the distances between similar substituents in compounds analogous to 5, suggesting that distances between metal binding sites can be varied by rational choice of the tripodal triamine. Guest solvent molecules occupy the central cavity and grooves between the arms of $H_6L$. The THF guest within the cavity forms hydrogen bonds with two amides on one pyridine dicarboxamide arm with N—H•••O bond distances of 2.35(3) and 2.14(3) Å and angles of 146(3)° and 158(3)°, which are comparable to those for interactions between THF and other amides.[14] The four remaining amides from the other pyridine dicarboxamide arms form hydrogen bonds with THF and water molecules, all of which occupy the grooves between ligand arms.

Treatment of a THF solution of $H_6L$ with potassium hexamethyldisilazide followed by ferric chloride at −78° C. afforded the dark red-brown trianionic [(FeCl$_2$)$_3$L]$^{3-}$ complex. In ESI(−)/MS of the product solution,[15] ions corresponding to triiron(III) complexes are observed including the potassium adduct of the parent complex, K[(FeCl$_2$)$_3$L]$^{2-}$, as well as species in which one or more chloride ligands are substituted for hydroxide. In the UV/visible spectrum of the product complex, we observe a strong absorption band centred at 294 nm ($\epsilon$=43,900 $M^{-1}cm^{-1}$) and a broad feature in the visible region (524 nm, $\epsilon$=3,980 $M^{-1}cm^{-1}$). These absorption maxima are comparable to those reported for other ferric complexes of substituted pyridine-2,6-dicarboxamides.[16,17] Attempts to deprotonate the $H_6L$ with stronger bases, such as methyllithium, were unsuccessful and afforded only a mixture of products. Although related triarylmethanes undergo oxidation via formal hydride loss at the methine carbon atom,[10b] $^1$H-NMR spectra of reaction mixtures suggest that this proton can be abstracted by stronger bases, subsequently leading to ligand decomposition.

Figure 2:
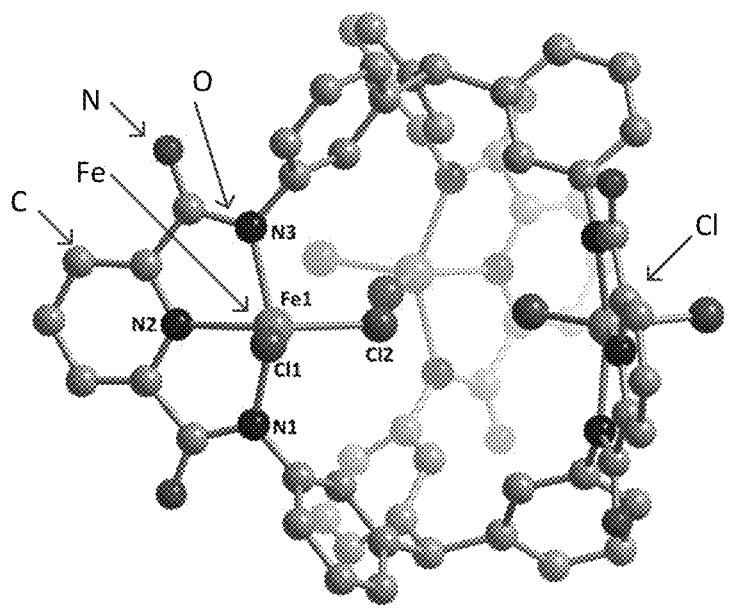
FIG. 2 illustrates a portion of the crystal structure of $[K(MeCN)_2]_3[(FeCl_2)_3L]$.
Figure 3:
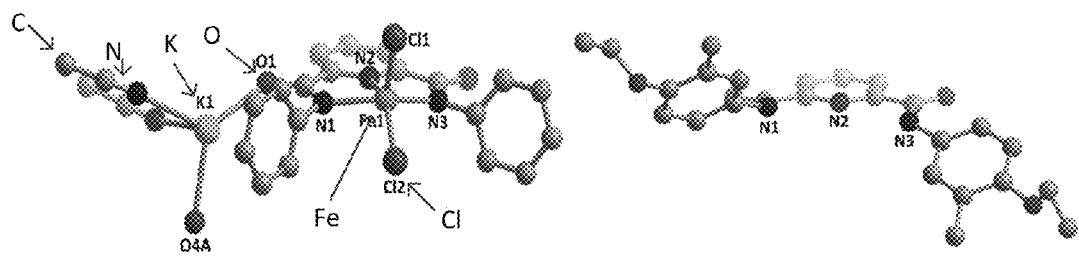
FIG. 3 illustrates a portion of crystal structures of $[K(MeCN)_2]_3[(FeCl_2)_3L]$ and $H_6L.(THF)_3.(H_2O)_3$ depicting structural changes upon metal binding.

Diffusion of diethyl ether into an acetonitrile solution of the product afforded dark red-brown crystals of $[K(MeCN)_2]_3[(FeCl_2)_3L]$ (FIG. 2). In the molecular structure of the complex, the iron-iron distance is 6.723(2) Å and the distance between the chloride donors housed within the interior of the complex is 3.413(3) Å. Each potassium cation is coordinated by two acetonitrile molecules from the crystallization solvent and two oxygen donors—one from an amide and the other from the ethoxy group on an adjacent ligand arm (FIG. 3, O1 and O4A). From the large metal-metal distances and absence of bridging ligands between the iron centres, we expected minimal electronic communication between the metal centres in the complex.

The steric demands of $H_6L$ enforce a 1:1 stoichiometry for each pyridine-2,6-dicarboxamide donor and iron(III) cation, which has not been realized for monometallic ferric complexes employing phenyl-substituted pyridine-2,6-dicarboxamide ligands.[16-18] In $[(FeCl_2)_3L]^{3-}$, each arm coordinates one iron(III) with the metal adopting a slightly distorted square pyramidal coordination geometry ($\tau$=0.05 with a 0.9% tetragonal distortion[19]) (FIG. 3). The basal plane is comprised of the pyridyl N-atom, two deprotonated carboxamides and one chloride anion, with an axial chloride donor completing the primary coordination sphere. The metal ion sits 0.570(2) Å above the $N_3Cl$ plane, comparable to other square pyramidal iron(III) complexes with $N_3$-donor sets.[20] The $N_{amide}$—Fe bond distances of 2.064(5) and 2.104(5) A and the $N_{amide}$—Fe—$N_{amide}$ bond angle of 145.1(2)° are similar to those reported for the high-spin $[Fe(PyPSMe)_2]^-$ complex.[17] Consistent with these structural similarities to the high-spin complex, a room temperature magnetic moment of 10.08 $\mu_B$ was determined for $[(FeCl_2)_3L]^{3-}$ by Evan's method using the parallel field formula,[21] which agrees with three S=3/2 ferric ions. Coordination of the $K^+$ cation to O1 likely weakens the donor strength of N1, and results in the longer $N_{amide}$—Fe bond distance as compared to N3-Fe bond.

Comparison of the structures of the $[(FeCl_2)_3L]^{3-}$ and the as-synthesized ligand reveals a significant structural change upon metal binding. In $H_6L$, both triphenoxymethane caps have the same chirality and the amide groups in each arm are not coplanar with either the pyridyl or phenyl rings (FIG. 3, right). Consequently, the angles between the planes of neighbouring pyridyl and phenyl aromatic rings are 36° and 50°, with almost an up-down conformation for the two phenyl rings relative to the pyridyl one. After deprotonation and metallation however, the angles between these aromatic ring planes increase to 75° and 83° with concomitant reorganization from the helical arrangement in $H_6L$ to one in which the two triphenoxymethane caps adopts opposite propeller conformations (FIGS. 2 and 3). The almost perpendicular disposition of the pyridyl ring versus the two neighbouring phenyl rings in $[(FeCl_2)_3L]^{3-}$ is consistent with that observed for monometallic complexes of substituted N,N'-diphenylpyridine-2,6-dicarboxamide.[16,17] This structural change consequently rotates the equatorial chloride away from the interior cavity, and could be an important feature for substrate access and/or product egress in future efforts. The significant ligand reorganization after metallation is reminiscent of the conformational changes observed during catalytic turnover in many enzyme systems[22] as well as the structural changes reported for molecular devices.[23] Methods to exploit this rearrangement to enhance reactivity or to respond to external stimuli are currently being explored.

Figure 4:
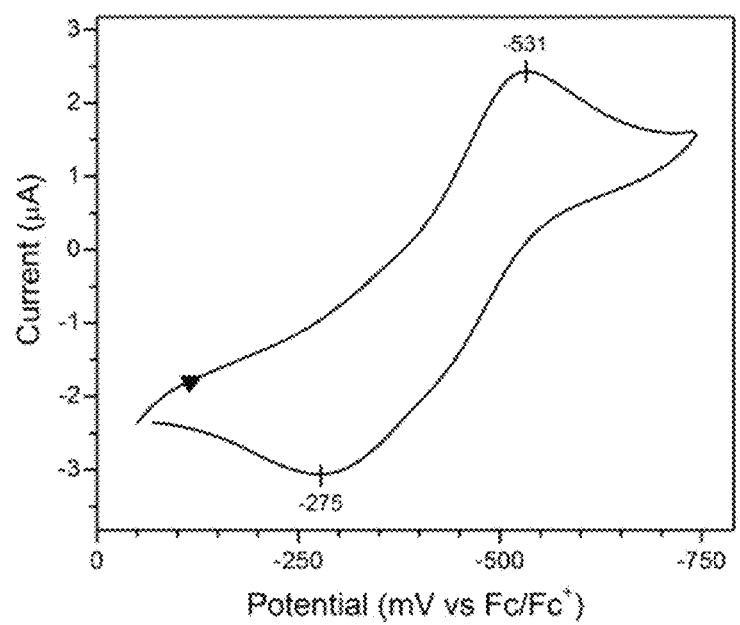
FIG. 4 illustrates a cyclic voltammogram of $[K(MeCN)_2]_3[(FeCl_2)_3L]$.

The cyclic voltammogram of $[K(MeCN)_2]_3[(FeCl_2)_3L]$ in anhydrous DMF shows a quasi-reversible response with $E_{1/2}$=−403 mV (vs. $Fc/Fc^+$) assigned to the $Fe^{III}/Fe^{II}$ couple, which is comparable to the value reported by Mukherjee and co-workers for a bis(pyridine-2,6-dicarboxamido)iron(III) complex (FIG. 4).[16] The large $\Delta E_p$ of 256 mV is consistent with a structural change upon reduction,[24] although we cannot discount weak electrostatic coupling between the metal centres, which may give rise to three overlapping waves. No change was observed in the amplitude of either the cathodic or anodic waves after repeated scanning, suggesting that there is no ligand or complex decomposition during the reaction. Electrochemical data collected on $H_6L$ and the potassium salt of $L^{6-}$, which was generated in situ with KHMDS, support our assignment of this process as metal-based. From magnetic susceptibility measurements on $[K(MeCN)_2]_3[(FeCl_2)_3L]$, the saturation value of $\chi_M T$ at room temperature of 7.4 emu·K·$mol^{-1}$ is comparable to the expected theoretical value for three isolated S=3/2 iron(III) centres.

In conclusion, we have reported the synthesis and characterization of a tris(hydroxyphenyl)methane-based cryptand and its corresponding trianionic triiron(III) complex. For the former, the ligand arms preassemble a central void space, capable of accommodating guest species. The triiron(III) complex serves as an synthetic proof of principle as the metal cations decorate the internal cavity, and are primed to react cooperatively with a bound substrate. Although the metal centers appear to be site-isolated in the iron(III) complex, we are exploring routes to displace the equatorial chloride ligands to allow substrates to bind and bridge the metal centres and turn on cooperativity. Preliminary work suggests that the chloride-chloride distance depends on the metal oxidation state, opening the possibility of designing complexes as redox-dependent host-guest systems.

References, each of which is incorporated herein by reference:

1. a) S. Iwata, C. Ostermeier, B. Ludwig, and H. Michel, Nature, 1995, 376, 660-669; b) T. Tsukihara, H. Aoyama, E. Yamashita, T. Tomizaki, H. Yamaguchi, K. Shinzawa-Itoh, R. Nakashima, R. Yaono, and S. Yoshikawa, Science, 1995, 269, 1069-1074; c) T. Tsukihara, H. Aoyama, E. Yamashita, T. Tomizaki, H. Yamaguchi, K. Shinzawa-Itoh, R. Nakashima, R. Yaono, and S. Yoshikawa, Science, 1996, 272, 1136-1144; d) R. L. Lieberman and A. C. Rosenzweig, Nature, 2005, 434, 177-182; e) R. A. Himes, K. Barnese, and K. D. Karlin, Angew. Chem. Int. Ed., 2010, 49, 6714-6716; f) C. E. Tinberg and S. J. Lippard, Acc. Chem. Res., 2011, 44, 280-288.
2. a) E. C. Brown, J. T. York, W. E. Antholine, E. Ruiz, S. Alvarez, and W. B. Tolman, J. Am. Chem. Soc., 2005, 127, 13752-13753; b) W. Nam, Acc. Chem. Res., 2007, 40, 522-531; c) D. Huang and R. H. Holm, J. Am. Chem. Soc., 2010, 132, 4693-4701; d) E. M. Gale, A. C. Simmonett, J. Telser, H. F. Schaefer, and T. C. Harrop, Inorg. Chem., 2011, 50, 9216-9218; e) M. T. Kieber-Emmons, Y. Li, Z. Halime, K. D. Karlin, and E. I. Solomon, Inorg. Chem., 2011, 50, 11777-11786.

3. T. Heinisch and T. R. Ward, Curr. Opin. Chem. Biol., 2010, 14, 184-199.
4. H. Chen, W. S. Weiner, and A. D. Hamilton, Curr. Opin. Chem. Biol., 1997, 1, 458-466.
5. A. P. Umali and E. V. Anslyn, Curr. Opin. Chem. Biol., 2010, 14, 685-692.
6. a) Q. Lu, J. J. Reibenspies, A. E. Martell, and R. J. Motekaitis, Inorg. Chem., 1996, 35, 2630-2636; b) S. Carvalho, C. Cruz, R. Delgado, M. G. B. Drew, and V. Félix, Dalt. Trans., 2003, 4261; c) M. Boiocchi, M. Bonizzoni, L. Fabbrizzi, G. Piovani, and A. Taglietti, Angew. Chem., 2004, 116, 3935-3940; d) B. Verdejo, J. Aguilar, A. Domenech, C. Miranda, P. Navarro, H. R. Jiménez, C. Soriano, and E. García-España, Chem. Comm., 2005, 3086; e) P. Mateus, R. Delgado, P. Brandão, and V. Félix, Chem.-Eur. J., 2011, 17, 7020-7031.
7. a) J. M. Lehn, S. H. Pine, E. Watanabe, and A. K. Willard, J. Am. Chem. Soc., 1977, 99, 6766-6768; b) J. P. Collman, J. E. Hutchison, M. A. Lopez, and R. Guilard, J. Am. Chem. Soc., 1992, 114, 8066-8073; c) E. Kim, E. E. Chufán, K. Kamaraj, and K. D. Karlin, Chem. Rev., 2004, 104, 1077-1134; d) C. J. Chang, Z.-H. Loh, C. Shi, F. C. Anson, and D. G. Nocera, J. Am. Chem. Soc., 2004, 126, 10013-10020; e) G. E. Alliger, P. Müller, L. H. Do, C. C. Cummins, and D. G. Nocera, Inorg. Chem., 2011, 50, 4107-4115; f) P. Mateus, R. Delgado, F. Lloret, J. Cano, P. Brandão, and V. Félix, Chem.-Eur. J., 2011, 17, 11193-11203.
8. M. Sun, T. Xu, W. Gao, Y. Liu, Q. Wu, Y. Mu, and L. Ye, Dalt. Trans., 2011, 40, 10184.
9. M. B. Dinger and M. J. Scott, Inorg. Chem., 2001, 40, 856-864.
10. a) M. B. Dinger and M. J. Scott, Eur. J. Org. Chem., 2000, 2000, 2467-2478; b) M. B. Dinger and M. J. Scott, J. Chem. Soc. Perk. T. 1, 2000, 1741-1748; c) M. B. Dinger and M. J. Scott, Inorg. Chem., 2000, 39, 1238-1254; d) P. C. Hillesheim, Thesis, University of Florida, 2010.
11. J. Rosevear and J. Wilshire, Aust. J. Chem., 1985, 38, 1163.
12. (a) A. P. Bisson, V. M. Lynch, M.-K. C. Monahan, and E. V. Anslyn, Angew. Chem. Int. Ed., 1997, 36, 2340-2342. (b) G. Hennrich and E. V. Anslyn, Chem. Eur. J., 2002, 8, 2218-2224.
13. A. L. Spek, Acta Crystallogr. D, 2009, 65, 148-155.
14. M. C. Etter, Z. Urbanczyk-Lipkowska, M. Zia-Ebrahimi, and T. W. Panunto, J. Am. Chem. Soc., 1990, 112, 8415-8426.
15. D. M. Chisholm, A. G. Oliver, and J. S. McIndoe, Dalt. Trans., 2010, 39, 364.
16. M. Ray, D. Ghosh, Z. Shirin, and R. Mukherjee, Inorg. Chem., 1997, 36, 3568-3572.
17. T. C. Harrop, L. A. Tyler, M. M. Olmstead, and P. K. Mascharak, Eur. J. Inorg. Chem., 2003, 2003, 475-481.
18. a) D. S. Marlin, M. M. Olmstead, and P. K. Mascharak, Inorg. Chem., 1999, 38, 3258-3260; b) S. Ghosh, B. Roehm, R. A. Begum, J. Kut, M. A. Hossain, V. W. Day, and K. Bowman-James, Inorg. Chem., 2007, 46, 9519-9521; c) A. P. Singh and R. Gupta, Eur. J. Inorg. Chem., 2010, 2010, 4546-4554; d) N. P. Chmel, L. E. N. Allan, J. M. Becker, G. J. Clarkson, S. S. Turner, and P. Scott, Dalt. Trans., 2011, 40, 1722.
19. A. W. Addison, T. N. Rao, J. Reedijk, J. van Rijn, and G. C. Verschoor, J. Chem. Soc. Dalton, 1984, 1349-1356.
20. A. Boudier, P.-A. R. Breuil, L. Magna, C. Rangheard, J. Ponthus, H. Olivier-Bourbigou, and P. Braunstein, *Organometallics*, 2011, 30, 2640-2642.
21. a) D. F. Evans, J. Chem. Soc., 1959, 2003; b) S. Sur, J. Mag. Res. (1969), 1989, 82, 169-173; c) E. M. Schubert, J. Chem. Ed., 1992, 69, 62; d) G. A. Bain and J. F. Berry, J. Chem. Ed., 2008, 85, 532.
22. (a) K. Henzler-Wildman and D. Kern, Nature, 2007, 450, 964-972. (b) P. Bernadó and M. Blackledge, Nature, 2010, 468, 1046-1048.
23. E. R. Kay, D. A. Leigh, and F. Zerbetto, Angew. Chem. Int. Ed., 2007, 46, 72-191.
24. G. N. Di Francesco, G. L. Guillet, and L. J. Murray, unpublished results.

Experimental

General Considerations. All reactions were performed under dry, air free condition using standard Schlenk techniques or in an Innovative Technologies glovebox unless otherwise noted. Solvents were either purchased anhydrous and used as received (Sigma-Aldrich) or extracted from an Innovative Technologies solvent purification system. NMR spectra were recorded on either a 500 Mhz Inova or 300 Mhz Mercury spectrophotometer with the spectra referenced to the residual protonated solvent signal, 7.27 ppm for $CDCl_3$-$d_1$ and 1.94 for $CH_3CN$-$d_3$. Deuterated solvents were purchased from Cambridge Isotope Labs and dried by standard methods as described elsewhere.[1] Infrared spectra were recorded as solids on a Bruker Vertex 80v FTIR using a Pike GladiATR stage. UV/VIS spectra were recorded on a Varian Cary 50 UV/VIS spectrophotometer using screw-top quartz cuvettes with a 1 cm path-length. X-Ray Intensity data were collected at 100 K on a Bruker DUO diffractometer using MoKα radiation (λ=0.71073 Å) or CuKα radiation(λ=1.54178 Å) from an ImuS power source, and an APEXII CCD area detector. Raw data frames were read by the SAINT[2] program and integrated using 3D profiling algorithms. The resulting data were reduced to produce hkl reflections and their intensities and estimated standard deviations. The data were corrected for Lorentz and polarization effects and numerical absorption corrections were applied based on indexed and measured faces. The structure was solved and refined in SHELXTL6.1, using full-matrix least-squares refinement.[3] The non-H atoms were refined with anisotropic thermal parameters and all of the H atoms were calculated in idealized positions and refined riding on their parent atoms unless otherwise stated. Cyclic voltammetry was performed under a nitrogen atmosphere using a standard three electrode setup. Electrodes were purchased from either BASi, Inc. or CH Instruments, Inc. Potential sweeps were controlled by a Princeton Applied Research Versastat II potentiostat. Magnetic data were acquired using a Quantum Design MPMS XL superconducting quantum interference device (SQUID) magnetometer. 10.28 mg of $[K(MeCN)_2]_3[(FeCl_2)_3L]$ microcrystals were introduced in a 0.273 ml PE sample vial along with about 20 mg of 1-eicosene. Once in the magnetometer, the vial was heated to 308 K for 10 minutes (1-eicosene mp=303 K) at 0 Gauss in order to homogenize the sample and 1-eicosene mixture before data were collected. The sample is cooled down from room temperature to 5K (10 K $min^{-1}$) in an applied field of 100 Gauss (field-cooled, FC) or zero Gauss (zero field-cooled, ZFC). Magnetization is measured while warming from 5 K to 300 K and then expressed in terms of magnetic susceptibility. Mass spectra were recorded on an Agilent 6210 TOF mass spectrometer by introducing samples into the MS by direct infusion. Samples were dissolved in anhydrous solvent in septum capped vials and transferred to the MS with a 10 μL syringe. All data were processed using MassHunter™ software. Elemental analyses were performed by Complete Analysis Laboratories, Inc (Parsippany, N.J.). 2,6-Pyridinedicarboxylic acid chloride purchased from Sigma Aldrich was purified by vacuum sublimation prior to use. 4-(tert-butyl)-2-isopropylphenol (1) and 5-(tert-butyl)-2-hydroxy-3-isopropylbenzaldehyde (2) were synthesized according to literature procedures.[4,5] All other reagents were purchased from Sigma-Aldrich and used without further purification.

6,6',6"-methanetriyltris(4-(tert-butyl)-2-isopropylphenol) (3). Compound 3 was synthesized as described elsewhere with minor modifications.[6] Briefly, a sample of 5-(tert-butyl)-2-hydroxy-3-isopropylbenzaldehyde (2) (5.08 g, 24.3 mmol) was combined with 2 equivalents of 4-(tert-butyl)-2-isopropylphenol (1) (9.17 g, 47.7 mmol) and 14 mL of methanol in a 100 mL schlenk flask. With a sodium carbonate trap connected to the reaction flask, the reaction mixture was cooled to 0° C. and thionyl chloride (11.4 mL, 157.7 mmol) was added dropwise causing an immediate change from orange/yellow to dark purple for the reaction mixture. The reaction was stirred overnight. The precipitate that was formed was collected by filtration. The residue was recrystallized from hexanes to afford 3 as a pale purple solid (6.88 g) in 48% yield with respect to the starting salicylaldehyde. $^1$H NMR (CDCl$_3$-d) δ ppm 1.20 (27 H, s), 1.26 (18 H, d, J=6.9 Hz), 3.22 (3 H, spt, J=6.9 Hz), 4.91 (3 H, s), 5.83 (1 H, s), 6.81 (3 H, d, J=2.3 Hz), 7.18 (3 H, d, J=2.3 Hz). $^{13}$C-{$^1$H} NMR, δ 22.7, 27.5, 31.4, 34.3, 41.8, 122.2, 123.7, 125.7, 135.0, 143.5, 148.9. Anal. calcd. for C$_{40}$H$_{58}$O$_3$: C, 81.86; H, 9.96; N, 0.00. Found: C, 81.79; H, 10.32; N, 0.00.

Tris(2-ethoxy-3-isopropyl-5-nitrophenyl)methane (4). A dry 250 mL Schlenk flask was charged with 3 (9.17 g, 15.6 mmol) and anhydrous dimethylformamide (120 mL). The resulting solution was cooled to 0° C. NaH (1.24 g, 51.5 mmol) was added under N$_2$ flow, followed by addition of ethyl iodide (4.1 mL, 51 mmol) via syringe, and the reaction allowed to warm to room temperature overnight. Saturated aqueous NH$_4$Cl was added to neutralize remaining NaH which generated a white precipitate. The precipitate was isolated by filtration and thoroughly rinsed with water, and subsequently recrystallized from methanol to yield tris(5-(tert-butyl)-2-ethoxy-3-isopropylphenyl)methane as a white crystalline solid (6.83 g) in 65% yield. $^1$H NMR (CDCl$_3$-d) δ ppm 1.17 (s, 27 H), 1.20 (d, J=6.8 Hz, 18 H), 1.30 (t, J=7.1 Hz, 9 H), 3.28 (spt, J=7.1 Hz, 3 H), 3.55 (q, J=7.1 Hz, 6 H), 6.59 (s, 1 H), 6.77 (d, J=2.3 Hz, 3 H), 7.07 (d, J=2.5 Hz, 3 H). $^{13}$C-{$^1$H} NMR, δ 15.7, 24.2, 26.6, 31.4, 34.3, 38.6, 69.3, 120.4, 125.7, 136.8, 140.6, 145.2, 152.1. Anal. calcd. for C$_{46}$H$_{70}$O$_3$: C, 82.33; H, 10.51; N, 0.00. Found: C, 82.27; H, 10.86; N, 0.00. A portion of the crystalline material (9.19 g, 13.7 mmol) was dissolved in dichloromethane (48 mL) in a 250 mL round-bottom flask. To this solution was added trifluoroacetic acid (9.4 mL, 123.3 mmol), causing a sudden color change to red. Concentrated nitric acid (7.9 mL, 125 mmol) was then slowly added to the reaction mixture. After stirring overnight, the solvent and trifluoroacetic acid were removed in vacuo from the bright orange reaction mixture. Methanol (112 mL) was added inducing precipitation of the crude product. The resulting suspension was cooled to approximately 0° C., filtered, and rinsed with cold methanol, giving 4 as a yellow powder (7.43 g, 85% yield). $^1$H NMR (CDCl$_3$-d) δ ppm 1.26 (9 H, t, J=6.8 Hz), 1.27 (18 H, d, J=6.8 Hz), 3.27 (3 H, spt, J=6.8 Hz), 3.51 (6 H, q, J=6.9 Hz), 6.71 (1 H, s), 7.64 (3 H, d, J=2.8 Hz), 8.14 (3 H, d, J=2.8 Hz). $^{13}$C-{$^1$H} NMR, δ 15.4, 23.6, 27.1, 38.8, 70.5, 122.3, 122.5, 137.3, 144.3, 144.6, 159.8. Anal. calcd. for C-34H$_{43}$N$_3$O$_9$: C, 64.03; H, 6.80; N, 6.59. Found: C, 63.67; H, 6.78; N, 6.30.

5,5',5"-methanetriyltris(4-ethoxy-3-isopropylaniline) (5). In a three-neck round-bottom flask, a sample of 4 (3.63 g, 5.69 mmol) was dissolved in a solution of EtOH/THF (25/180 mL). Rainey nickel (~100 mg) was added to the mixture, which was then degassed by the freeze-pump-thaw method and the flask was backfilled with anhydrous H$_2$ gas. The reaction was stirred at room temperature under a constant H$_2$ stream for two days and then filtered to remove the Rainey nickel The solvent was removed under reduced pressure. The residue was dissolved in diethyl ether and extracted with a 10% HCl solution (3×, 50 mL). The aqueous phase was washed with hexanes (3×50 mL) followed by addition of 2 M NaOH to a final pH of 10. The precipitated solid was extracted into dichloromethane (3×50 mL). The combined organics were dried with sodium sulfate and the volatiles removed under reduced pressure. The residue was then recrystallized from methanol yielding 2.53 g (81%) of 5 as a colorless crystalline solid. $^1$H NMR (CDCl$_3$-d) δ ppm 1.14 (18 H, d, J=6.9 Hz), 1.19 (9 H, t, J=7.0 Hz), 3.09 (6 H, br. s.), 3.21 (3 H, spt, J=6.9 Hz), 3.38 (6 H, q, J=6.9 Hz), 6.26 (3 H, d, J=2.9 Hz), 6.37 (3 H, d, J=2.7 Hz), 6.51 (1 H, s). $^{13}$C-{$^1$H} NMR, δ 15.5, 24.0, 26.3, 38.4, 69.4, 111.1, 115.2, 138.9, 141.6, 142.9, 147.3. Anal. calcd. for C$_{34}$H$_{49}$N$_3$O$_3$: C, 74.55; H, 9.02; N, 7.67. Found: C, 74.26; H, 9.24; N, 7.59.

Di-(N2,N2',N2"-(methanetriyltris(4-ethoxy-3-isopropylbenzene-5,1-diyl)))tris(pyridine-2,6-dicarboxamide) (H$_6$L)

In a Schlenk flask, 5 (2.67 g, 4.88 mmol) was dissolved in 100 mL of THF. The flask was fitted with an addition funnel containing 2,6-pyridinedicarboxylic acid chloride (1.49 g, 7.31 mmol) dissolved in 35 mL of THF. The reaction vessel was cooled to 0° C. and the acid chloride solution was added dropwise over approximately 40 minutes. The reaction was allowed to warm to room temperature and stirred overnight. The solvent was removed from the reaction under reduced pressure and the resulting residue was purified by passage over a plug of silica gel (20:1 DCM:THF) yielding a pale yellow solid after removal of solvent. The resulting residue was further purified by crystallization in slowly evaporating THF yielding H$_6$L as a colorless crystalline solid (1.78 g, 48%). Single crystals suitable for x-ray diffraction studies were grown by diffusion of pentane into a THF solution of H$_6$L. $^1$H NMR (CDCl$_3$-d) δ ppm 1.14-1.20 (36 H, m), 1.31 (18 H, d, J=6.9 Hz), 3.26 (7 H, spt, J=6.8 Hz), 3.36 (6 H, m, J=8.8, 7.1 Hz), 3.83 (6 H, m, J=8.9, 7.1 Hz), 6.30 (6 H, d, J=2.7 Hz), 6.43 (2 H, s), 8.07 (3 H, t, J=7.8 Hz), 8.34 (6 H, d, J=2.6 Hz), 8.42 (6 H, d, J=7.8 Hz), 8.88 (6 H, s). $^{13}$C-{$^1$H} NMR, δ 15.8, 24.0, 24.4, 27.1, 40.7, 69.9, 119.0, 119.2, 126.0, 133.3, 138.4, 139.5, 143.6, 150.2, 152.0, 162.1. Sample analyzed as 5.(H$_2$O)$_2$. Anal. calcd. for C$_{89}$H$_{105}$N$_9$O$_{14}$: C, 70.10; H, 6.94; N, 8.27. Found: C, 70.10; H, 6.95; N, 8.14.

[K(MeCN)$_2$]$_3$[(FeCl$_2$)$_3$L].(THF)$_2$. A portion of H$_6$L (203.6 mg, 0.1368 mmol) was dissolved 10 mL of THF and cooled to −78° C. A solution of KHMDS (180.2 mg, 0.9032 mmol) in 2 mL of THF was also cooled to −78° C. and then added dropwise to the solution of H$_6$L causing an immediate change from a colorless to a yellow solution. The reaction was stirred for approximately 30 minutes during which time a solution of FeCl$_3$ (73.3 mg, 0.452 mmol) was made in a minimum volume of THF and cooled to −78° C. The FeCl$_3$ solution was added dropwise to the yellow reaction mixture causing an immediate change to a dark red-brown solution. The reaction was stirred overnight, then filtered and the solvent was removed under vacuum. The residue was dissolved in a minimal volume of acetonitrile, precipitated with diethyl ether and the precipitate collected by filtration. Crystallization was afforded by a bulk diffusion of Et$_2$O into acetonitrile to yield black microcrystalline powder. Single crystals for x-ray diffraction were grown by a slow diffusion of diethyl ether into a solution of the complex in acetonitrile. (−)ESI-MS (DMF): 951.9 m/z, [K(FeCl$_2$)$_3$L]$^{2-}$. Anal. calcd. for C$_{97}$H$_{111}$Cl$_6$Fe$_3$K$_3$N$_9$O$_{14}$: C, 54.84; H, 5.27; N, 5.93. Found: C, 54.53; H, 5.16; N, 5.78.

Example 2

[K(18-crown-6)]$_2$[(FeCl)$_3$KL] (6). A portion of H$_6$L (203.6 mg, 0.1368 mmol) and KH (37.0 mg, 0.9032 mmol) were dissolved in 10 mL of THF and allowed to stir at room temperature for 6 h. 18-crown-6 (119 mg, 0.452 mmol) was then added to the reaction mixture followed by dropwise addition of a solution of FeCl$_2$ (57.3 mg, 0.452 mmol) in THF (~2 mL). The dark-red solution reaction was stirred overnight, then filtered, and the solvent was removed under vacuum. The residue was dissolved in a minimal volume of acetonitrile, precipitated with diethyl ether and the precipitate collected by filtration to afford the target complex in 72% yield (237 mg).

Figure 5:
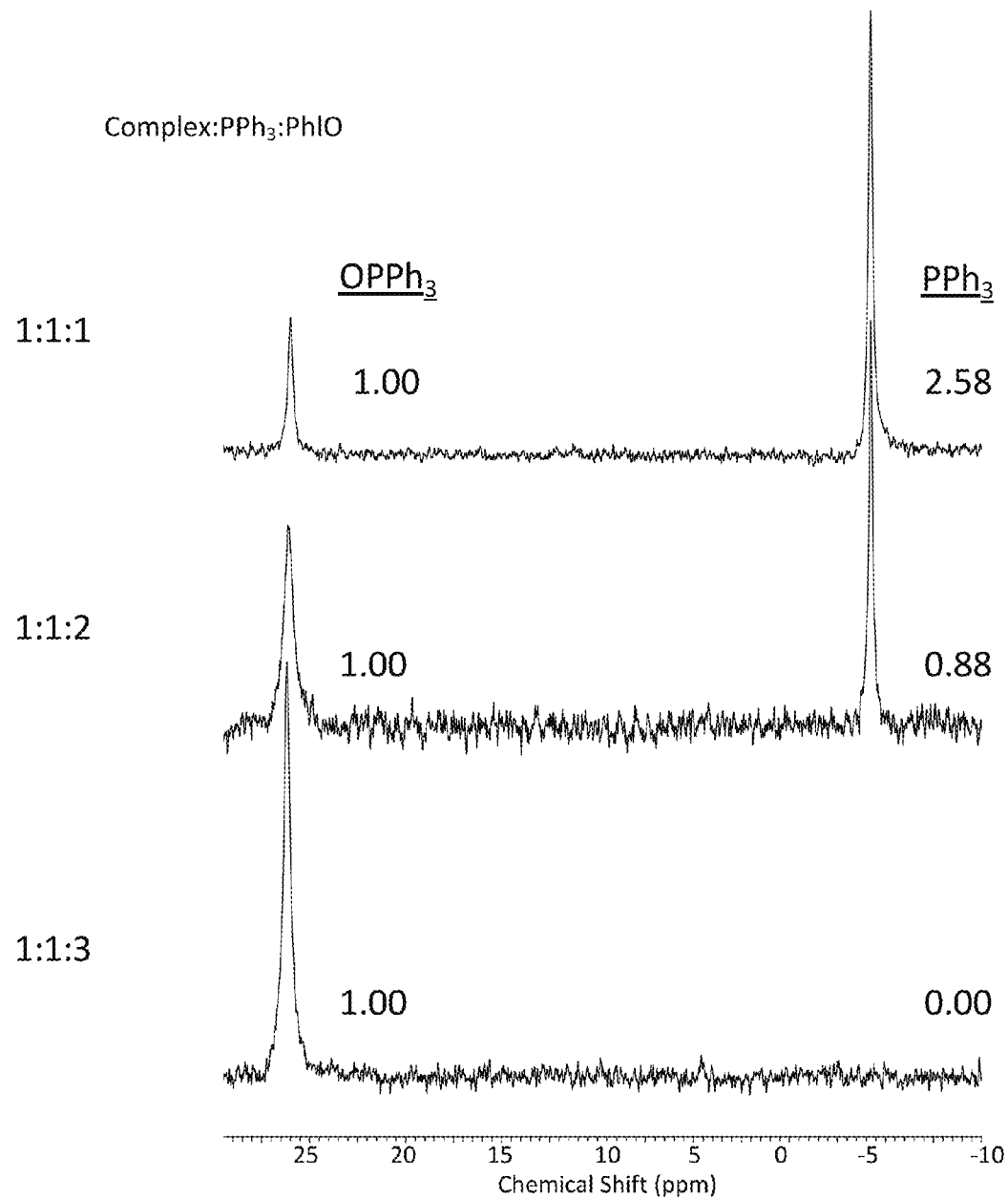
FIG. 5 illustrates a 5 $^{31}$P-NMR spectra for O-atom transfer from PhIO to $Ph_3P$ by 6.

O-Atom Transfer Using 6 and Iodosobenzene. A solution of 6 (20.5 mg, 7.69 µmol) and triphenylphosphine (20.2 mg, 7.70 µmol) was made in dry, air-free acetonitrile (7 mL). Either one, two, or three equivalents of PhIO were added and the reaction stirred for 6 h at room temperature. The solvent was then removed and the residue dissolved in d$_6$-benzene and the ratio of triphenylphosphine oxide to triphenylphosphine in the product mixture was determined by $^{31}$P-NMR. Percent conversion of starting phosphine to the phosphine oxide increased with increasing equivalents of PhIO, with complete conversion observed for three equivalents (FIG. 5). FIG. 5 illustrates $^{31}$P-NMR spectra in d$_6$-benzene of the products from the reaction of 6 with iodosobenzene and triphenyl phosphine. Complete conversion of Ph$_3$P to Ph$_3$PO is achieved with three equivalents of iodosobenzene relative to both complex 6 and Ph$_3$P.

Example 3

Brief Introduction: Incorporating pendant hydrogen bonding interactions in the design of metal complexes provides a controlled method for coupling electron and proton transfer steps. This effect can dramatically lower the activation barrier for processes such as dioxygen activation or carbon dioxide reduction. Using our approach to assemble multimetallic complexes, we have developed a robust method for incorporating two metal ions selectively and simultaneously assemble a hydrogen bonding network throughout the internal cavity of the complex. These complexes sequester atmospheric carbon dioxide as synthesized, and are expected to be electrocatalysts for carbon dioxide reduction.

Figure 6:
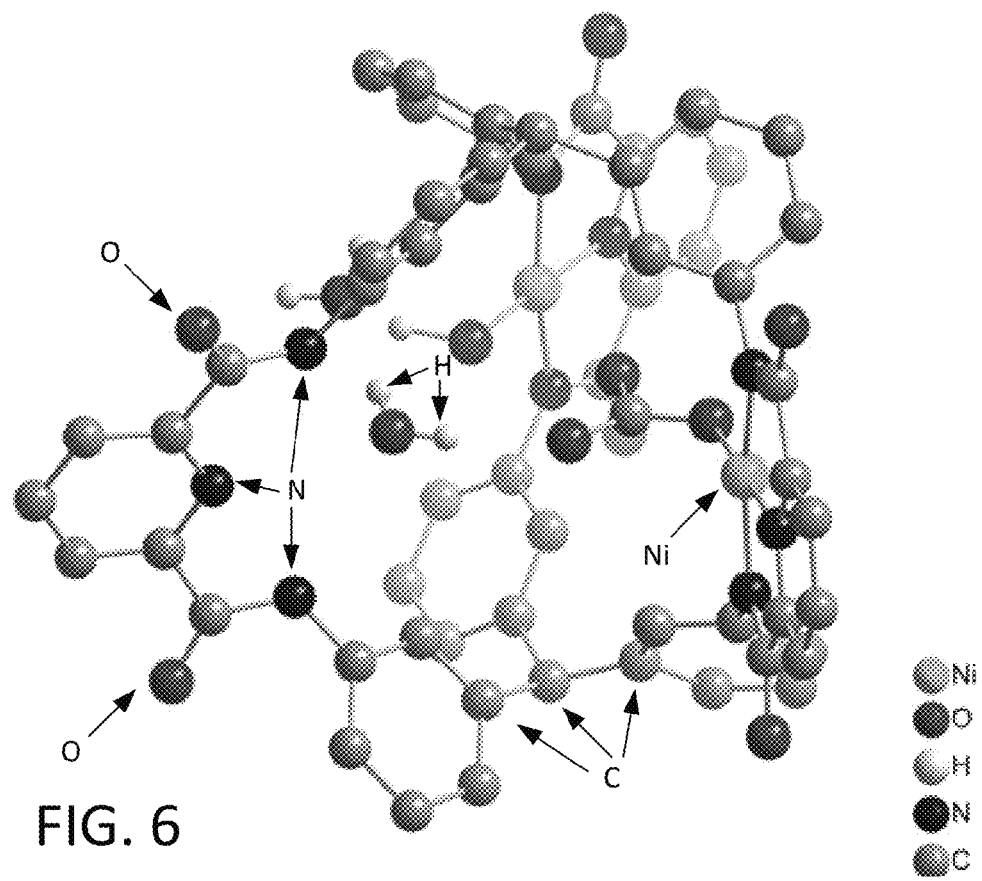
FIG. 6 illustrates a portion of the crystal structure of $Ni_2Na$.

Experimental:

(Et$_4$N)$_2$[Ni(OH)Ni(HCO$_3$)H$_2$L].THF.H$_2$O (7). A sample of H$_6$L (90.3 mg, 0.0610 mmol) was dissolved in 25 mL of tetrahydrofuran (THF). Two equivalents of Ni(OTf)$_2$.2MeCN (53.22 mg, 0.121 mmol) was added to the solution, causing a color change from colorless to pale green. Dropwise addition of 1.5 M Tetraethylammonium hydroxide in methanol (0.250 mL, 0.367 mmol) led to an immediate color change to red. The reaction was stirred overnight. The reaction mixture was filtered over celite, and the solvent removed under vacuum. The red solid was taken up in 25 mL of dichloromethane, washed twice with 20 mL of 1M NaOH, and the solution dried with anhydrous magnesium sulfate. The mixture was filtered through celite and placed under vacuum to be dried overnight. The compound was then recrystallized by diffusion of diethyl ether into a THF solution forming red blocks of 7 in 68% yield. The x-ray crystal structure of 7 is depicted in FIG. 6. FIG. 6 illustrates a portion of the crystal structure of 7. Two water molecules are ordered within the cavity by hydrogen bonding interactions with the bicarbonate and hydroxide ligands on the nickel ions, and to the two amide protons on the unmetallated arm.

$^1$H NMR (500 MHz, CHLOROFORM-d) δ ppm 0.96-1.16 (m, 49 H) 1.17-1.24 (m, 18 H) 1.27 (d, J=6.59 Hz, 8 H) 2.63 (br. s., 8 H) 2.82-2.91 (m, 3 H) 2.97 (br. q, J=6.90, 6.90, 6.90 Hz, 16 H) 3.13 (s, 4 H) 3.20-3.35 (m, 6 H) 3.53 (br. spt, J=7.40, 7.40, 7.40, 7.40, 7.40, 7.40 Hz, 2 H) 3.66 (spt, J=7.40 Hz, 2 H) 3.70-3.78 (m, 2 H) 6.55 (s, 2 H) 6.58 (d, J=2.06 Hz, 2 H) 6.78 (d, J=2.06 Hz, 2 H) 6.81 (d, J=2.06 Hz, 2 H) 6.91 (d, J=2.06 Hz, 2 H) 6.99 (d, J=2.20 Hz, 2 H) 7.51 (d, J=7.69 Hz, 2 H) 7.54 (d, J=7.69 Hz, 2 H) 7.70 (d, J=2.33 Hz, 2 H) 7.78 (t, J=7.70 Hz, 1 H) 7.83 (t, J=7.69 Hz, 1 H) 7.98 (t, J=7.82 Hz, 1 H) 8.27 (d, J=7.69 Hz, 2 H) 11.33 (s, 2 H). $^{13}$C NMR (126 MHz, CHLOROFORM-d) δ ppm 7.36 (br. s.) 15.54 (s) 15.62 (s) 15.68 (s) 23.55 (s) 23.60 (s) 23.75 (s) 24.20 (s) 24.41 (s) 24.67 (s) 26.37-26.41 (m) 26.47 (d) 40.23 (s) 53.00 (s) 68.76-68.85 (m) 69.75 (s) 69.88 (s) 119.20 (s) 121.47-121.57 (m) 121.98-122.05 (m) 122.22-122.26 (m) 123.84-123.89 (m) 125.21-125.27 (m) 125.54-125.61 (m) 125.73-125.79 (m) 126.53-126.62 (m) 132.93 (s) 137.72-137.78 (m) 138.18 (s) 138.68-138.73 (m) 140.81-140.87 (m) 141.03 (s) 141.33 (s) 141.75 (s) 141.85 (s) 142.14-142.21 (m) 150.38 (s) 151.91 (s) 151.95 (s) 152.01 (s) 152.28 (s) 152.46 (s) 159.23-159.27 (m) 163.65 (s) 167.69-167.78 (m)

Alternate method for synthesizing 7.

A sample of H$_6$L (50.6 mg, 0.034 mmol) was dissolved in approximately 10 mL of THF. A equivalent sample of Ni(OTf)$_2$.2MeCN (44.7 mg, 0.102 mmol) was added to the solution, causing a color change from colorless to pale green. Dropwise addition of 1.5 M Tetraethylammonium hydroxide in methanol (0.210 mL, 0.316 mmol) was added causing an immediate color change to red. The reaction was stirred and then filtered over celite followed by solvent removal under vacuum. The red solid was taken up in 10 mL dichloromethane and washed twice with 10 mL of 1M KOH. The combined organics were dried with magnesium sulfate, the solution filtered over celite, and then dried under vacuum overnight. The solid was dissolved in THF, and diethyl ether diffused into the solution to afford red crystals of 7 in 64% yield. $^1$H NMR (500 MHz, CHLOROFORM-d) δ ppm 0.98-1.16 (m, 57 H) 1.17-1.25 (m, 22 H) 1.27 (d, J=6.73 Hz, 8 H) 2.39 (br. s., 12 H) 2.80-2.88 (m, 3 H) 2.98 (br. q, J=7.10, 7.10, 7.10 Hz, 16 H) 3.07-3.18 (m, 4 H) 3.19-3.36 (m, 6 H) 3.51 (spt, J=7.50 Hz, 2 H) 3.66 (spt, J=7.60 Hz, 2 H) 3.70-3.78 (m, 2 H) 6.56 (s, 2 H) 6.59 (d, J=1.92 Hz, 2 H) 6.79 (d, J=2.33 Hz, 2 H) 6.81 (d, J=2.33 Hz, 2 H) 6.91 (d, J=2.33 Hz, 2 H) 7.00 (d, J=2.33 Hz, 2 H) 7.51 (d, J=7.69 Hz, 2 H) 7.54 (d, J=7.69 Hz, 2 H) 7.70 (d, J=2.47 Hz, 2 H) 7.78 (t, J=7.69 Hz, 1 H) 7.84 (t, J=7.69 Hz, 1 H) 7.99 (t, J=7.76 Hz, 1 H) 8.27 (d, J=7.82 Hz, 2 H) 11.32 (s, 2 H). $^{13}$C NMR (126 MHz, CHLOROFORM-d) δ ppm 7.38 (br. s.) 15.38-15.88 (m) 23.57 (br. s.) 23.71 (br. s.) 24.20 (s) 24.43 (s) 24.64 (br. s.) 26.33-26.60 (m) 30.92 (s) 40.19 (s) 53.04 (br. s.) 68.70 (br. s.) 69.73 (br. s.) 69.92 (br. s.) 119.05 (br. s.) 121.45 (s) 121.94 (br. s.) 122.33 (br. s.) 123.86 (br. s.) 125.20 (br. s.) 125.57 (br. s.) 125.67-125.87 (m) 125.91-126.19 (m) 126.69 (br. s.) 132.88 (s) 137.83 (s) 138.03 (br. s.) 138.27 (s) 138.72 (br. s.) 139.09 (s) 140.83 (s) 140.99 (s) 141.38 (s) 141.68 (s) 141.90 (s) 142.17 (br. s.) 150.36-150.52 (m) 151.84-151.94 (m) 152.08 (d) 152.34 (s) 152.57 (s) 159.35 (s) 163.66 (s) 167.72 (d)

Figure 7:
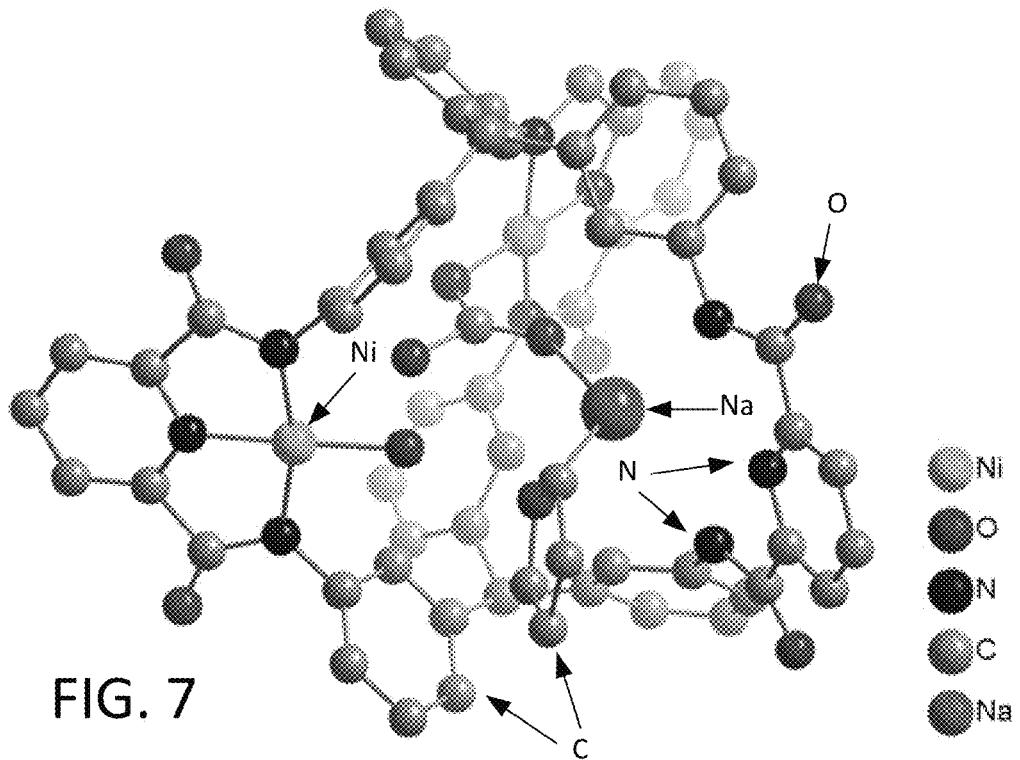
FIG. 7 illustrates a portion of the crystal structure of $Cu_3$.

(Et$_4$N)$_2$[Ni(OH)Ni(CO$_3$)NaH$_2$L].THF.H$_2$O (8). A sample of H$_6$L (50.6 mg, 0.034 mmol) was dissolved in approximately 10 mL of THF. A equivalent sample of Ni(OTf)$_2$.2MeCN (44.7 mg, 0.102 mmol) was added to the solution, causing a color change from colorless to pale green. Dropwise addition of 1.5 M Tetraethylammonium hydroxide in methanol (0.210 mL, 0.316 mmol) was added causing an immediate color change to red. The reaction was stirred and then filtered over celite followed by solvent removal under vacuum. The red solid was taken up in 10 mL dichloromethane and washed twice with 10 mL of 1M NaOH. The combined organics were dried with magnesium sulfate, the solution filtered over celite, and then dried under vacuum overnight. The solid was dissolved in THF, and diethyl ether diffused into the solution to afford red crystals of 8 in good yield. A portion of the structure of 8 determined by single-crystal X-ray diffraction is depicted in FIG. 7. FIG. 7 illustrates a portion of the crystal structure of 8. A sodium cation is installed within the cavity in place of the proton on the bicarbonate ligand in 7.

Figure 8:
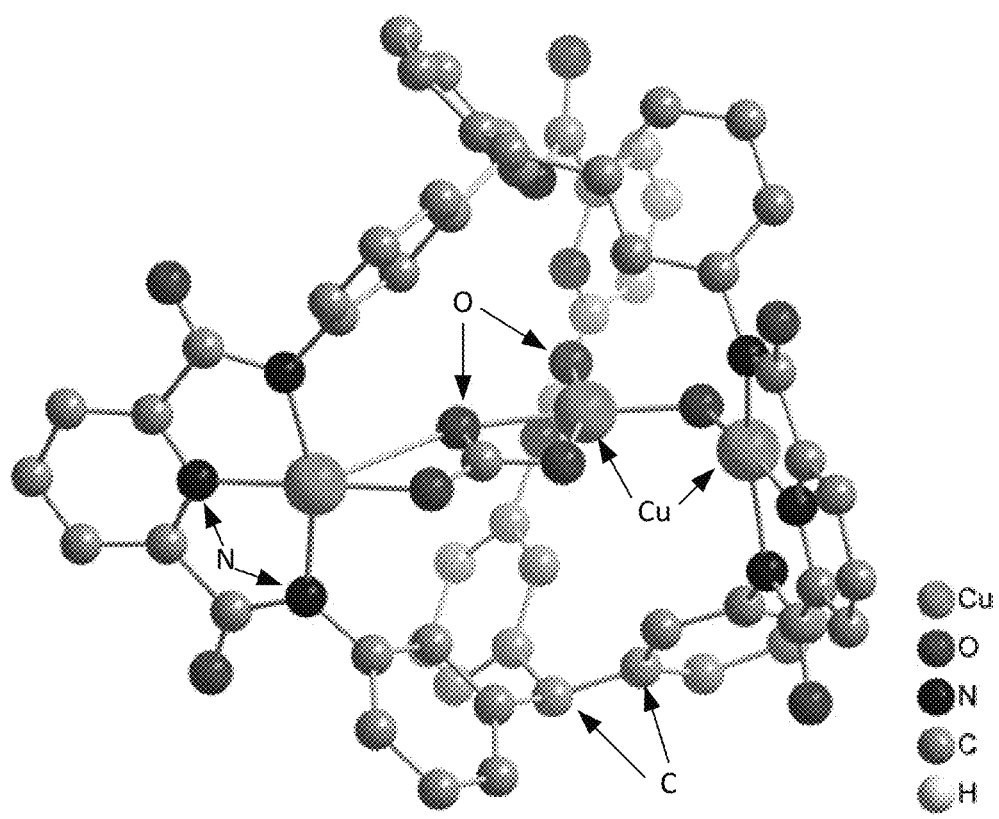
FIG. 8 illustrates a portion of the crystal structure of $(Et_4N)_2[Cu(\mu\text{-}OH)Cu(CO_3)Cu(OH)H_2L]$.

(Et$_4$N)$_2$[Cu(μ-OH)Cu(CO$_3$)Cu(OH)H$_2$L] (9). A sample of H$_6$L (50.6 mg, 0.034 mmol) was dissolved in approximately 10 mL of THF. A equivalent sample of Cu(OTf)$_2$ (36.9 mg, 0.102 mmol) was added to the solution, causing a color change from colorless to pale green. Dropwise addition of 1.5 M Tetraethylammonium hydroxide in methanol (0.210 mL, 0.316 mmol) was added causing an immediate color change to dark green. The reaction was stirred and then filtered over celite followed by solvent removal under vacuum. The green solid was taken up in 10 mL dichloromethane and washed twice with 10 mL of 1M KOH. The combined organics were dried with magnesium sulfate, the solution filtered over celite, and then dried under vacuum overnight, to afford the product as a green powder in good yield. A portion of the molecular structure of 9 is depicted in FIG. 8. FIG. 8 illustrates a portion of the crystal structure of 9. The structure is analogous to 8 where all cations in the structure are copper(II) centers.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to the measurement technique and the type of numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

At least the following is claimed:

1. A multimetallic assembly, comprising the following structure:

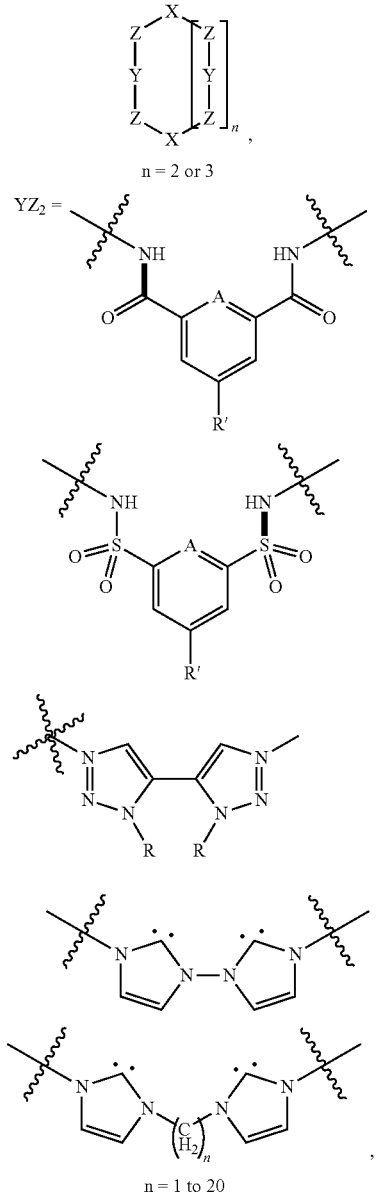

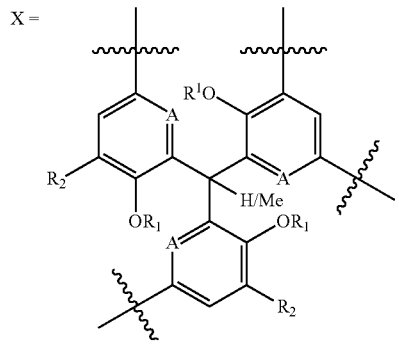

-continued

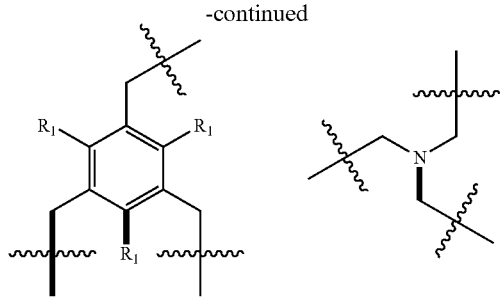

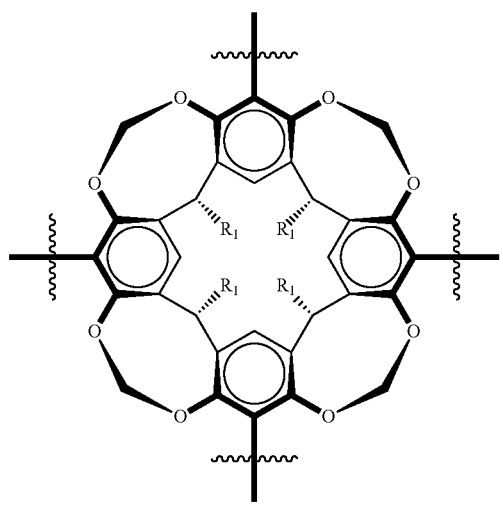

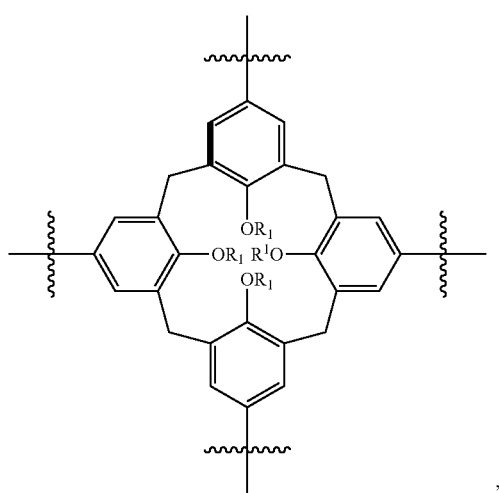

wherein Z is NH, NR, O, S, CH, CR, or $CH_2$; R and R' are independently selected from an alkyl group, an aryl group, $NO_2$, H, a substituted alkyl, a cycloalkyl, a substituted cycloalkyl, a substituted aryl, a heteroaryl, a substituted heteroaryl, a sulfonate, a sulfonyl ester, a carboxylate, an ester, $CF_3$, OMe, or $COOR_1$; A is CH or N; $R_1$ and $R_2$ are independently selected from H, alkyl group, an aryl group, a carboxylate, $NO_2$, a substituted alkyl, a cycloalkyl, a substituted cycloalkyl, a substituted aryl, a heteroaryl, a substituted heteroaryl, sulfone, sulfonate, a sulfonyl ester, a carboxylate, $CF_3$, OMe, or ester.

2. The multimetallic assembly of claim 1, wherein:

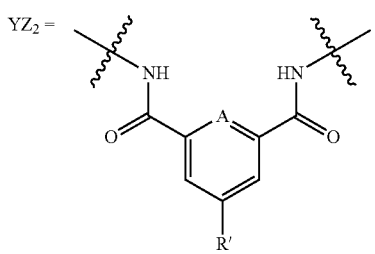

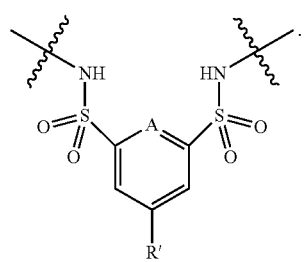

3. The multimetallic assembly of claim 1, wherein:

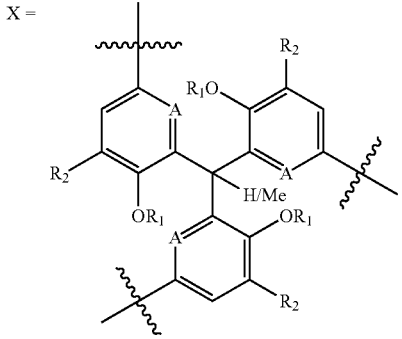

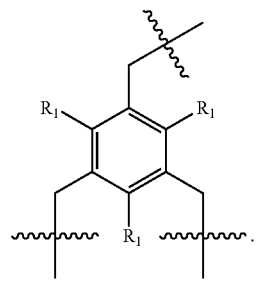

4. The multimetallic assembly of claim 1, wherein one or more metals are associated with the multimetallic assembly.

5. The multimetallic assembly of claim 2, wherein the metal is a transition metal.

6. The multimetallic assembly of claim 2, wherein the metal selected from the group consisting of: manganese, iron, cobalt, nickel, copper, vanadium, chromium, palladium, platinum, gold, ruthenium, rhodium, and iridium.

7. A method of oxidizing water, comprising:

exposing the water to a multimetallic assembly having the following structure:

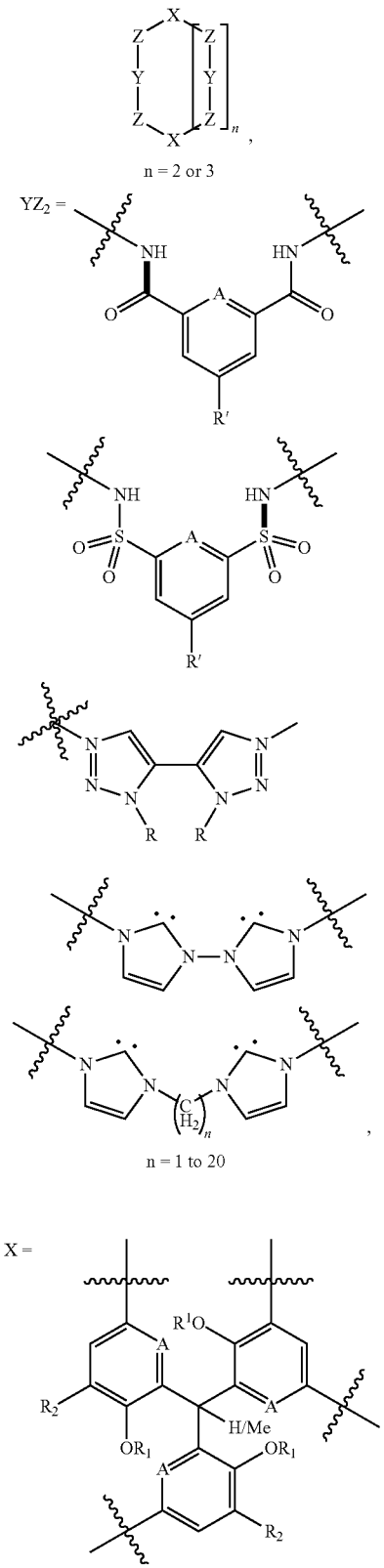

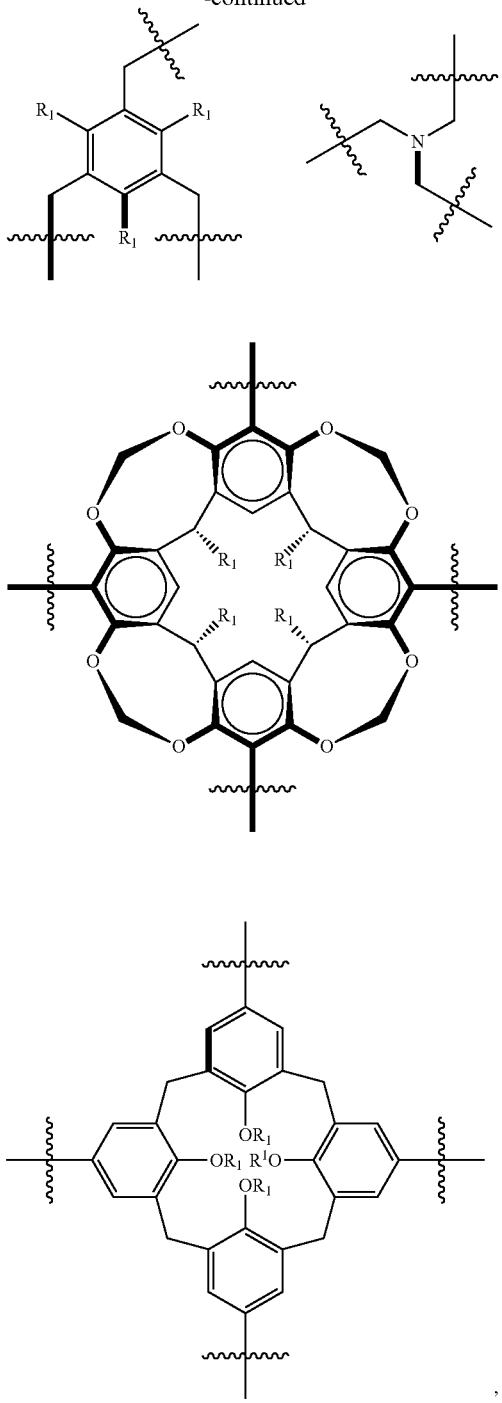

wherein Z is NH, NR, O, S, CH, CR, or $CH_2$; R and R' are independently selected from an alkyl group, an aryl group, $NO_2$, H, a substituted alkyl, a cycloalkyl, a substituted cycloalkyl, a substituted aryl, a heteroaryl, a substituted heteroaryl, a sulfonate, a sulfonyl ester, a carboxylate, an ester, $CF_3$, OMe, or $COOR_1$; A is CH or N; $R_1$ and $R_2$ are independently selected from H, alkyl group, an aryl group, a carboxylate, $NO_2$, a substituted alkyl, a cycloalkyl, a substituted cycloalkyl, a substituted aryl, a heteroaryl, a substituted heteroaryl, sulfone, sulfonate, a sulfonyl ester, a carboxylate, $CF_3$, OMe, or ester.

8. The multimetallic assembly of claim 7, wherein:

YZ₂ =

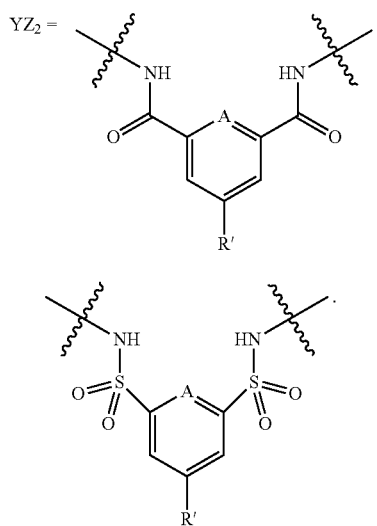

9. The multimetallic assembly of claim 7, wherein:

X =

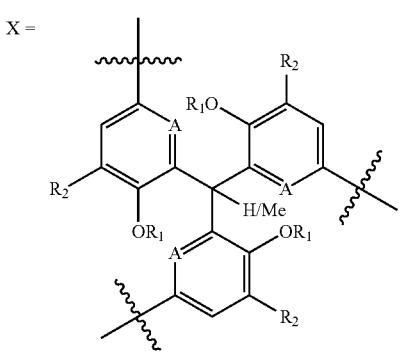

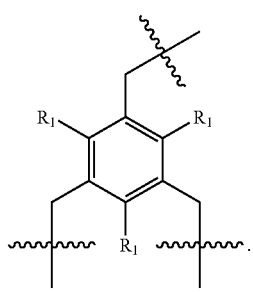

10. The multimetallic assembly of claim 7, wherein one or more metals are associated with the multimetallic assembly.

11. The multimetallic assembly of claim 10, wherein the metal is a transition metal.

12. The multimetallic assembly of claim 10, wherein the metal selected from the group consisting of: manganese, iron, cobalt, nickel, copper, vanadium, chromium, palladium, platinum, gold, ruthenium, rhodium, and iridium.

13. A method of reducing carbon dioxide, comprising:

exposing the carbon dioxide to a multimetallic assembly having the following structure:

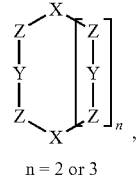

n = 2 or 3

YZ₂ =

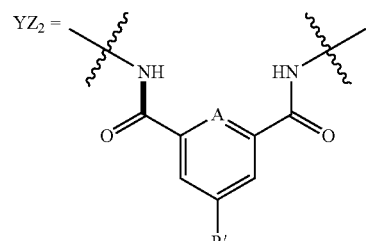

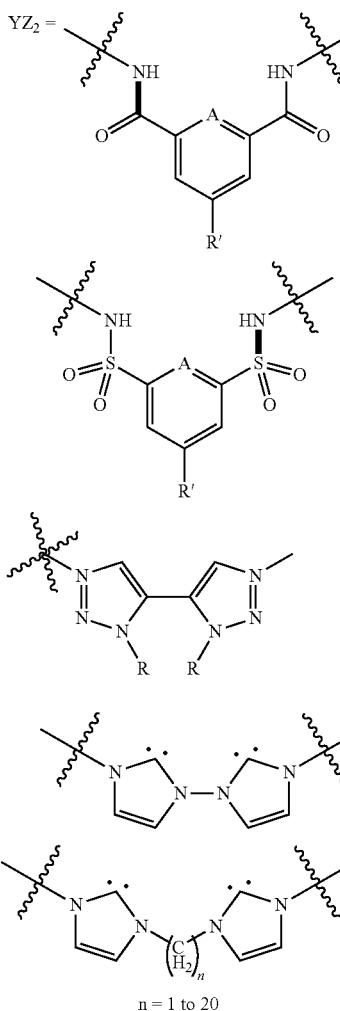

n = 1 to 20

X =

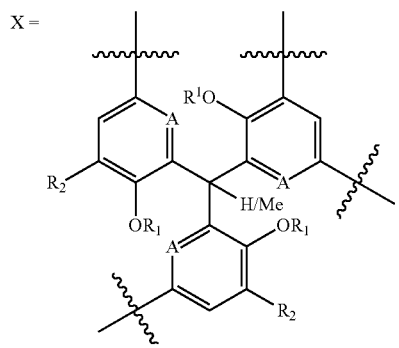

-continued

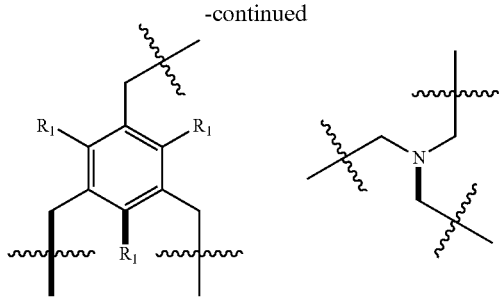

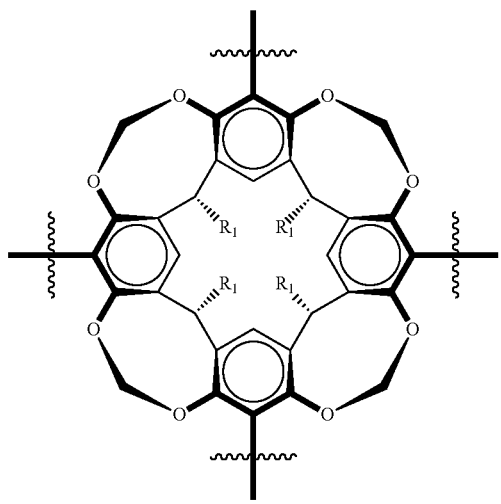

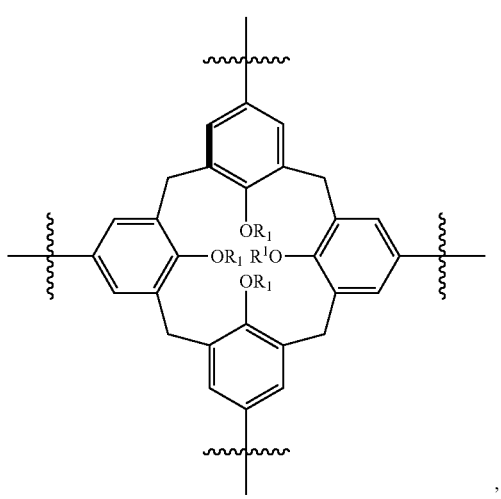

wherein Z is NH, NR, O, S, CH, CR, or CH$_2$; R and R' are independently selected from an alkyl group, an aryl group, NO$_2$, H, a substituted alkyl, a cycloalkyl, a substituted cycloalkyl, a substituted aryl, a heteroaryl, a substituted heteroaryl, a sulfonate, a sulfonyl ester, a carboxylate, an ester, CF$_3$, OMe, or COOR; A is CH or N; R$_1$ and R$_2$ are independently selected from H, alkyl group, an aryl group, a carboxylate, NO$_2$, a substituted alkyl, a cycloalkyl, a substituted cycloalkyl, a substituted aryl, a heteroaryl, a substituted heteroaryl, sulfone, sulfonate, sulfonyl esters, carboxylate, or ester.

14. A method of O-atom transfer, comprising:

exposing O$_2$ or a reactive oxygen species to a multimetallic assembly having the following structure:

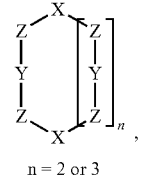

n = 2 or 3

YZ$_2$ =

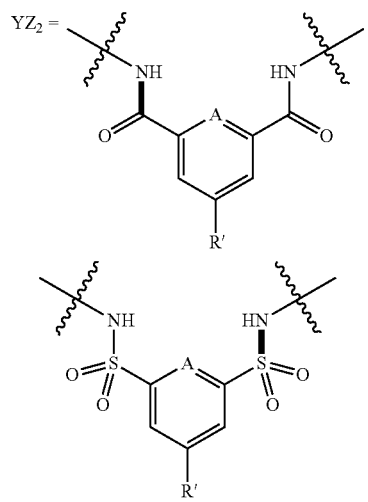

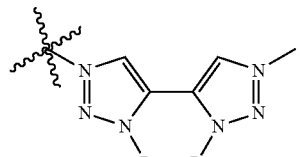

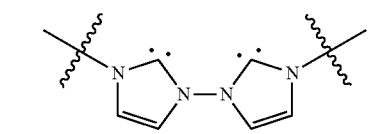

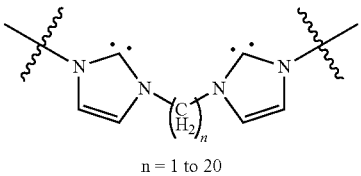

n = 1 to 20

X =

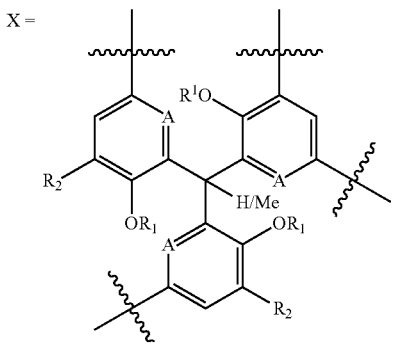

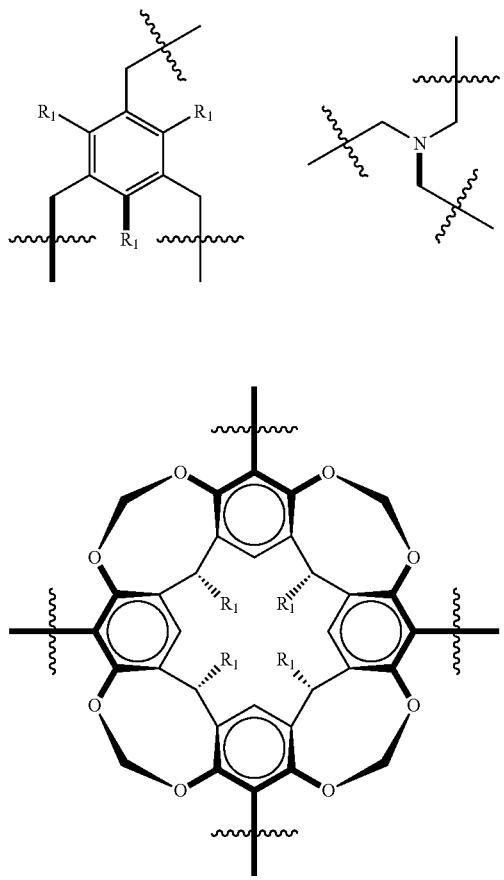

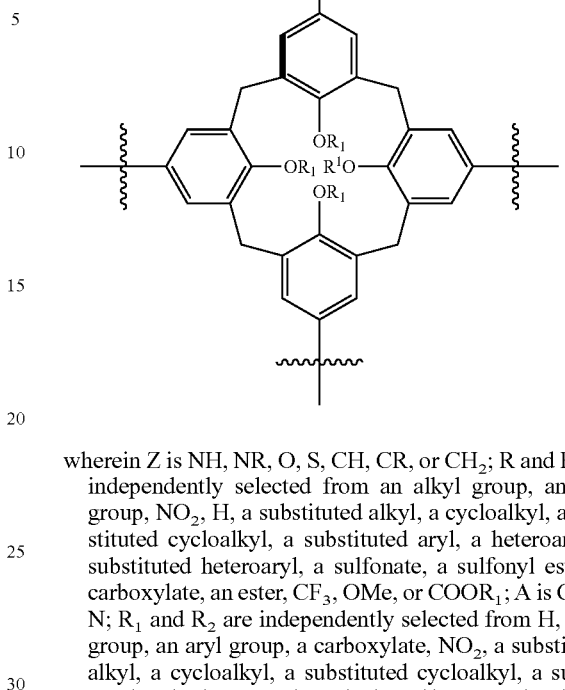

wherein Z is NH, NR, O, S, CH, CR, or $CH_2$; R and R' are independently selected from an alkyl group, an aryl group, $NO_2$, H, a substituted alkyl, a cycloalkyl, a substituted cycloalkyl, a substituted aryl, a heteroaryl, a substituted heteroaryl, a sulfonate, a sulfonyl ester, a carboxylate, an ester, $CF_3$, OMe, or $COOR_1$; A is CH or N; $R_1$ and $R_2$ are independently selected from H, alkyl group, an aryl group, a carboxylate, $NO_2$, a substituted alkyl, a cycloalkyl, a substituted cycloalkyl, a substituted aryl, a heteroaryl, a substituted heteroaryl, sulfone, sulfonate, a sulfonyl ester, a carboxylate, $CF_3$, OMe, or ester;

reacting the product of step one with an electron-rich substrate to transfer the O-atom to the electron-rich substrate.

\* \* \* \* \*